(12) United States Patent
Alsuhaibani

(10) Patent No.: US 11,541,182 B2
(45) Date of Patent: Jan. 3, 2023

(54) INTEGRATED SYRINGE AND GUIDEWIRE SYSTEM

(71) Applicant: ALSAHAB MEDICAL COMPANY L.L.C., Riyadh (SA)

(72) Inventor: Abdulaziz A. Alsuhaibani, Riyadh (SA)

(73) Assignee: ALSAHAB MEDICAL COMPANY, Riyadh (SA)

(*) Notice: Subject to any disclaimer, the term of this patent is extended or adjusted under 35 U.S.C. 154(b) by 327 days.

(21) Appl. No.: 16/846,430

(22) Filed: Apr. 13, 2020

(65) Prior Publication Data

US 2021/0213204 A1 Jul. 15, 2021

Related U.S. Application Data

(60) Provisional application No. 62/960,990, filed on Jan. 14, 2020.

(51) Int. Cl.
*A61M 5/31* (2006.01)
*A61M 5/315* (2006.01)

(52) U.S. Cl.
CPC ........ *A61M 5/3148* (2013.01); *A61M 5/3158* (2013.01); *A61M 5/31511* (2013.01); *A61M 5/31591* (2013.01); *A61M 2005/3131* (2013.01)

(58) Field of Classification Search
CPC ............ A61M 5/31511; A61M 5/3158; A61M 2005/3131; A61M 2205/583; A61M 2205/587
See application file for complete search history.

(56) References Cited

U.S. PATENT DOCUMENTS

| | | | |
|---|---|---|---|
| 1,221,103 A | | 4/1917 | Sorensen |
| 3,325,061 A | * | 6/1967 | Ellsworth ........... A61M 5/3137 |
| | | | D24/114 |
| 3,990,446 A | | 11/1976 | Taylor |
| 4,484,915 A | | 11/1984 | Tartaglia |
| 4,639,248 A | | 1/1987 | Schweblin |
| 4,813,433 A | | 3/1989 | Downey |
| 5,135,511 A | | 8/1992 | Houghton et al. |
| 5,582,595 A | | 12/1996 | Haber et al. |
| 5,814,023 A | | 9/1998 | Fulk et al. |
| 5,833,668 A | | 11/1998 | Aguilar |

(Continued)

FOREIGN PATENT DOCUMENTS

DE 20 2012 006 191 U1 8/2012
JP 2000-296178 A 10/2000
(Continued)

OTHER PUBLICATIONS

Application as filed in related U.S. Appl. No. 16/566,880 (now U.S. Publication No. US 2021/0038820 A1) filed Sep. 11, 2019, 29 pages.

(Continued)

*Primary Examiner* — Bradley J Osinski
(74) *Attorney, Agent, or Firm* — Xsensus LLP

(57) ABSTRACT

A syringe with an integrated guidewire tract. The tract provides a physical channel by which a guidewire is guided through the syringe structure. The syringe is configured to allow for a one-handed aspiration operation or injection operation, while freeing the other hand to move the guidewire through the guidewire tract of the syringe system.

29 Claims, 22 Drawing Sheets

(56) References Cited

U.S. PATENT DOCUMENTS

| | | | |
|---|---|---|---|
| 6,217,558 B1* | 4/2001 | Zadini | A61B 5/150244 |
| | | | 604/164.01 |
| 6,231,550 B1 | 5/2001 | Laughlin | |
| 6,368,308 B1* | 4/2002 | Nerney | A61M 5/31511 |
| | | | 604/218 |
| 2004/0073172 A1 | 4/2004 | Acha Gandarias | |
| 2005/0192543 A1 | 9/2005 | Sibbitt | |
| 2005/0215956 A1 | 9/2005 | Nerney | |
| 2006/0258990 A1 | 11/2006 | Weber | |
| 2011/0046604 A1 | 2/2011 | Felsovalyi et al. | |
| 2013/0131606 A1 | 5/2013 | Bertocci | |
| 2018/0008294 A1* | 1/2018 | Garrison | A61M 5/3129 |
| 2021/0038820 A1 | 2/2021 | Alsuhaibani | |

FOREIGN PATENT DOCUMENTS

| | | |
|---|---|---|
| JP | 2014-030559 A | 2/2014 |
| WO | 2020/012410 A1 | 1/2020 |

OTHER PUBLICATIONS

Application as filed in related U.S. Appl. No. 16/566,880, filed Sep. 11, 2019, 29 pages.

* cited by examiner

INTEGRATED SYRINGE AND GUIDEWIRE SYSTEM

CROSS REFERENCE TO RELATED APPLICATIONS

The present application includes subject matter related to that disclosed in U.S. patent application Ser. No. 16/566,880, filed in the US Patent and Trademark Office on Sep. 11, 2019, and in PCT Patent Application PCT/IB2019/055927, filed on Jul. 11, 2019, the entire contents of both of which being incorporated herein by reference. The present application also claims the benefit of the earlier filing date of, and claims priority under 35 U.S.C. § 119(e) to U.S. Provisional Application Ser. No. 62/960,990 filed in the US Patent and Trademark Office on Jan. 14, 2020, the entire contents of which being incorporated herein by reference.

BACKGROUND

Field of the Disclosure

The present disclosure generally relates to the field of medicine, including medical devices, as well as other fields where syringes may be used in aspiration and injection modes of operation was well as when employing a guidewire in a medical procedure.

Description of the Related Art

Medical syringes are used in both injection and aspiration modes. Conventionally, when a syringe is used to inject medicine (or other fluids) via a needle into a vein or the like, the operator holds the syringe in one hand and squeezes the plunger into the syringe cylinder using the thumb and fingers of the same hand. However, when a syringe is used to aspirate or withdraw blood or other fluid from a needle inserted in a vein or the like, the operator uses two hands, typically holding the cylinder in one hand while pulling the plunger out of the cylinder with the other hand.

Guidewires are devices used to enter tight spaces, such as obstructed valves or channels within a body, and/or to assist in inserting, positioning and moving a catheter. Guidewires vary in size, length, stiffness, composition, and tip shape.

Specialty syringes, such as that described in U.S. Pat. No. 4,484,915, have been made with multiple axially extending members that attach to a movable flange disposed at a forward end of the syringe. The flange is formed with circular opening into which a syringe body is inserted, which allows the fingers of the operator to apply a backward force (away from the forward end of the syringe) that is mechanically translated to the plunger. A fixed flange is fixedly included at the back end of the cylinder so the operator may place their thumb on the fixed flange to provide an oppositely oriented force to the force applied by the operator's fingers on the movable flange during an aspiration operation. During the aspiration operation, the movable flange is moved toward the fixed flange, and the multiple axial extending members move along an outer surface of the syringe.

SUMMARY

Various embodiments are described that integrate a guidewire tract into a syringe structure. The tract provides a physical channel by which a guidewire is guided through the syringe structure to the body. The syringe is configured to allow for a one-handed operation aspiration or injection operation, while freeing the other hand to move the guidewire through the guidewire tract of the syringe system and into the body.

The syringe for integrated aspiration and guidewire operations, includes a plunger, a barrel, and a guidewire tract integrated with at least one of the plunger and the barrel. The plunger may include a seal at a forward end thereof, a plunger push button at a rear end thereof, an internal plunger arm attached at a rear end thereof to the plunger push button and to the seal at a forward end thereof, and an external plunger arm attached at a rear end thereof to the plunger push button, the internal plunger arm being arranged co-axially with the external plunger arm and separated by a gap. A first flange extends radially away from the external plunger arm at the forward end thereof. The barrel may include a wall having a thickness that is accommodated by the gap, at least a portion of the wall being disposed in the gap between the internal plunger arm and external plunger arm, and a nozzle at a forward end thereof. A second flange extends radially away from the barrel at a rear end thereof. A guidewire tract integrated with at least one of the plunger and the barrel

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
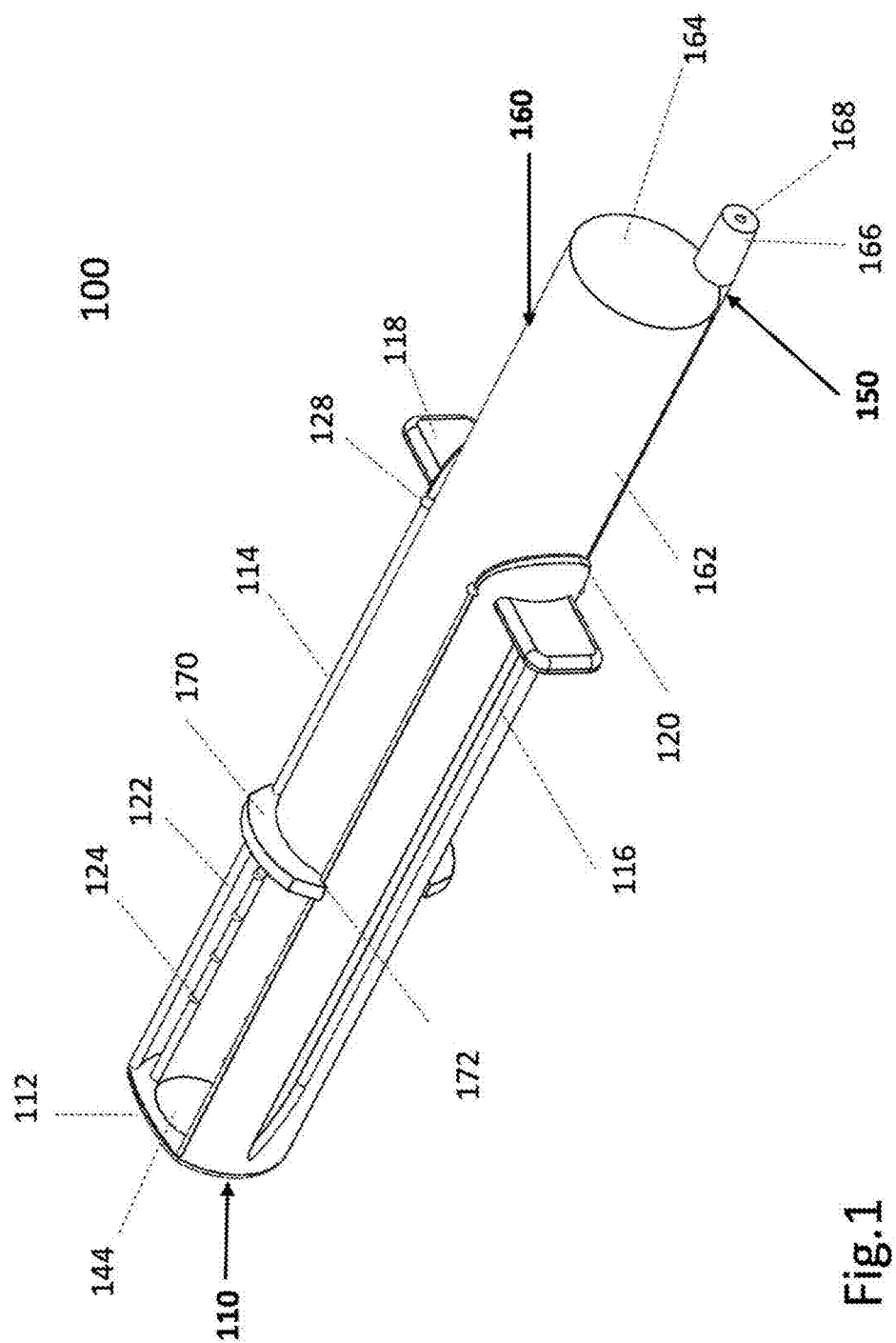
FIG. 1 is a perspective view of a syringe with an adapter for single-handed use of the syringe and including a guidewire tract according to a first embodiment.
Figure 2:
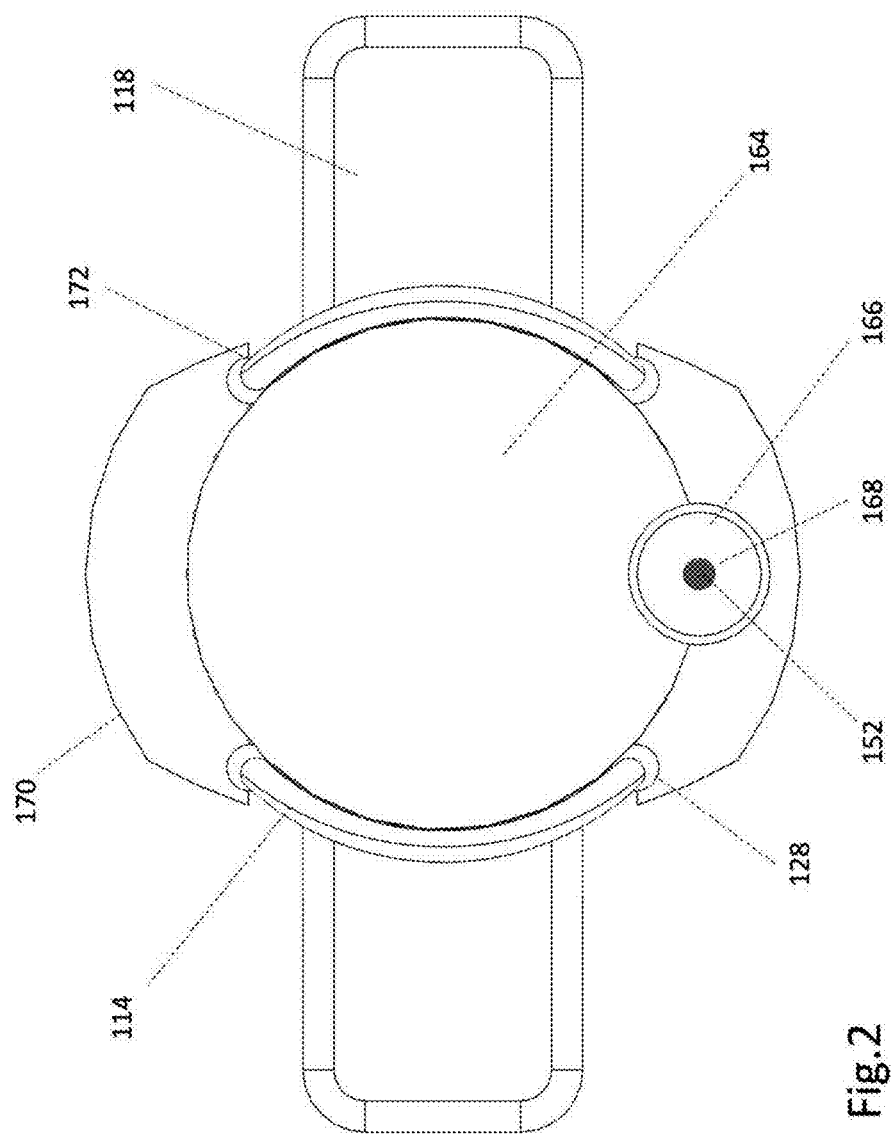
FIG. 2 is a front view of the syringe shown in FIG. 1 along a central longitudinal axis.
Figure 3:
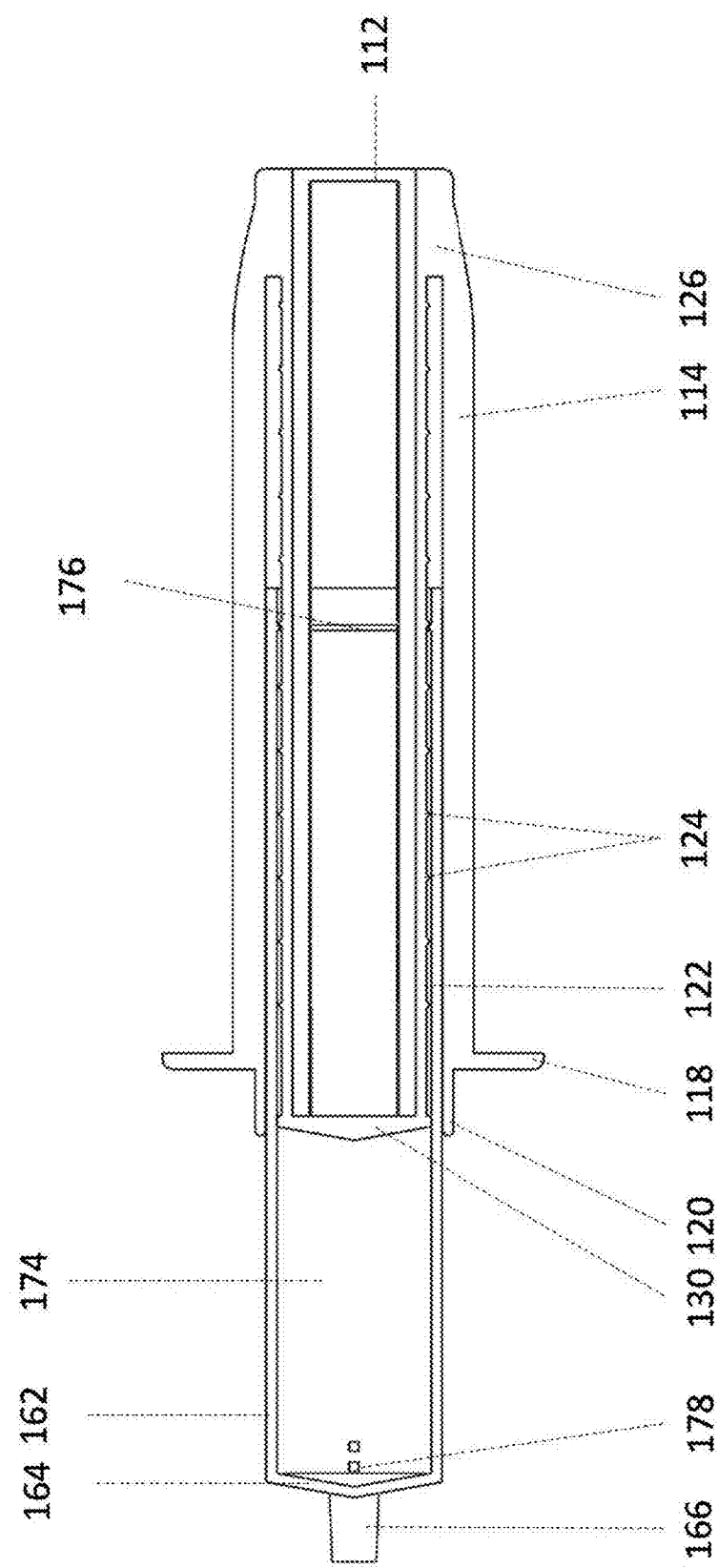
FIG. 3 is a cross-sectional view of the syringe shown in FIG. 1 along a central longitudinal axis.
Figure 4:
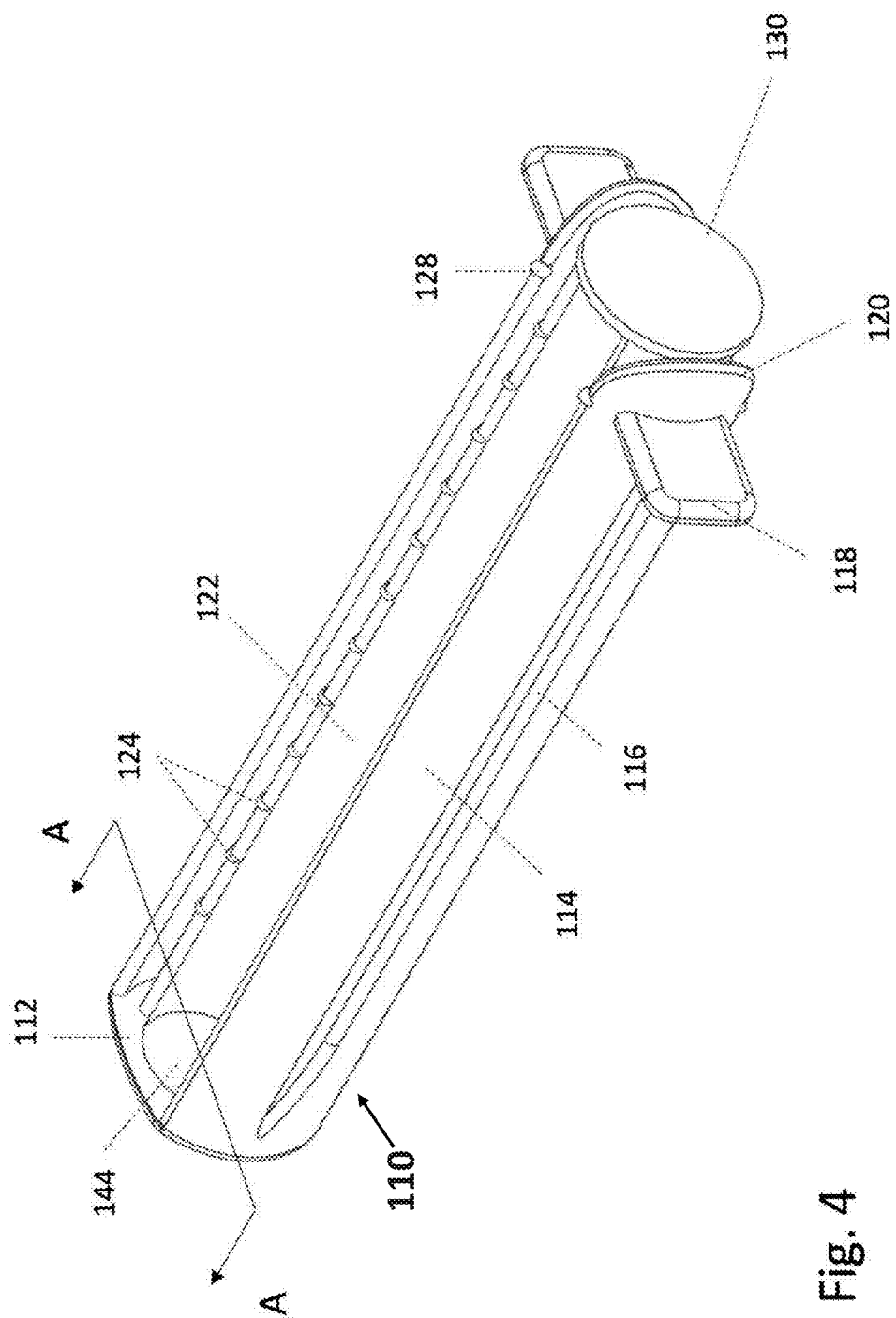
FIG. 4 is a perspective view of the plunger of the syringe of FIG. 1
Figure 5:
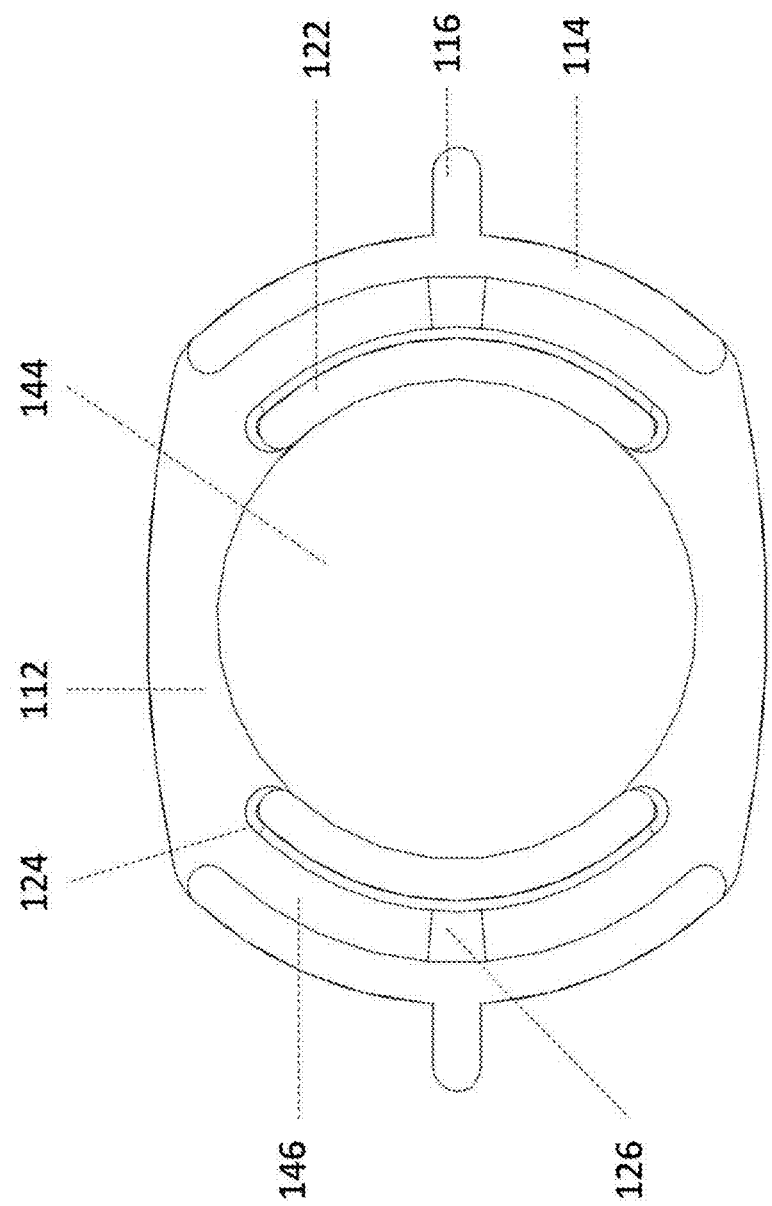
FIG. 5 is a cross-sectional view along A-A of the plunger of FIG. 4.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

The present inventor identified several suboptimal features about conventional syringes that are used for both injection and aspiration, as well as adapters that assist in aspiration. First, the inventor recognized that in conventional injection mode operator's normally clamp the barrel of the syringe between the operator's index finger and the middle finger, while depressing the plunger with the operator's thumb. However, a different gripping action is used for aspiration. Typically, aspiration is performed with two hands, one holding the body of the syringe, while the other grips the end of the plunger and withdraws the plunger from the body of the syringe. Two-handed operation is not ideal because the operator may very well want to use their other hand for another task, such as holding a bottle while withdrawing a sample.

The present inventor also recognized that physicians often use a syringe in the same medical procedures as using a guidewire, such as in a Seldinger technique. However, because the syringe often requires the use of two-hands, the attending physician cannot also adequately handle the insertions or retraction of a guidewire, without assistance.

In light of the recognition of this problem, the present inventor recognized the practical value in a syringe system that, in addition to enabling a singled-handed injection/aspiration function, can also incorporates a guidewire tract that assists the physician in deploying a guidewire into a body with the physician's other hand. Moreover, the present inventor recognized the value in have a syringe system that permitted a physician to be autonomous in a medical procedure requiring both a syringe and a guidewire.

Referring now to the drawings, wherein like reference numerals designate identical or corresponding parts throughout the several views, FIGS. 1 to 7 illustrate a syringe 100 for single-handed injection/aspiration operation with an integrated guidewire tract. The syringe 100 includes a plunger 110, a barrel 160, and a guidewire tract 150. During an injection operation, the plunger 110 is pressed towards a front end 164 of the barrel 160 to eject the contents (air, gas, or liquid) from the syringe cavity 174. During an aspiration operation, the plunger 110 is drawn away from the front end 164 of the barrel 160, so that a vacuum is created, and sample (air, gas, or a liquid) that is adjacent to an opening in the front end 164 is drawn into the syringe cavity 174.

The plunger 110 includes a pair of arms each including an external arm 114 and an internal arm 122, between which the barrel body 162 is to be inserted, connected by an arms connector 126 at a rear (posterior) portion thereof, e.g., a connector to strengthen the rear ends of each arm at its connection with push button 112. A push button 112 connects the arms connectors 126 for the pair of arms and serves as a thumb press for the syringe 100. The push button 112 may include an opening 144, e.g., a circular opening, for more thumb stability during injection. The inclusion of the opening 144 also reduces the material used for syringe and simplifies its manufacturability.

Each external arm 114 includes a first flange 118, e.g., forward flange or plunger flange. The first flange extends radially outward from each external arm 114 towards a front (anterior) end thereof in a first direction orthogonal to a longitudinal direction of the syringe 100. While the first flange 118 is illustrated as being part of the plunger 110, the first flange may be separate from the plunger 110. The first flanges 118 allow the operator to pull the plunger 110 backwards, e.g., during aspiration. For larger syringes, an additional flange may be in the middle of each external arm 114 and has similar design of first flange 118. Each external arm 114 may include an introducer 120 at the front end thereof to help assemble the plunger 110 with the barrel 160 during manufacturing. The introducer 120 may extend along the longitudinal direction towards the anterior to be adjacent to a seal 130 of the plunger 110. Each external arm 114 may include an external arm spine 116 that protrudes and extends in a longitudinal direction centrally along a majority thereof to strengthen the external arm 114, and a plunger stopper 128 on an outer surface adjacent to first flanges 118, that prevents the plunger 110 from falling out when the plunger 110 is pulled out to the maximum when stopper 128 contacts the inner surface of external arms passage 172.

Each internal arm 122 may have an arcuate shape in cross-section. An arms gap 146 (see FIG. 4) between the external arms 114 and the internal arms 122 is sufficient to accommodate a barrel body 162 of the barrel 160, as described below. Each internal arm 122 may include nubs 124 on protruding from outer surfaces, i.e., surfaces facing the barrel 160 but not the arms gap 146, to provide tactile sensation and feedback when the plunger moves in and out of a syringe cavity 174 and touching the inner circular prominence 176 of the barrel 160, e.g., depressing/retracting the plunger 110.

The internal arms 122 may be connected to each other by the seal 130 at the front end of the plunger 110. The seal 130 may be closer to the front end of the plunger 110 than the first flanges 118. When rear surface of the seal 130 contacts the inner circular prominence 176 of the barrel 160, it prevents the plunger 110 from falling out when the plunger is pulled out to the maximum, i.e., the seal 130 may also serve as a stopper, in addition to the stopper 128. A syringe seal 130 seals the air going inside or fluid going outside the syringe cavity 174. The syringe seal 130 may extend further in the syringe cavity 174 than the introducer 120 along an outside of the syringe cavity 174.

Figure 6:
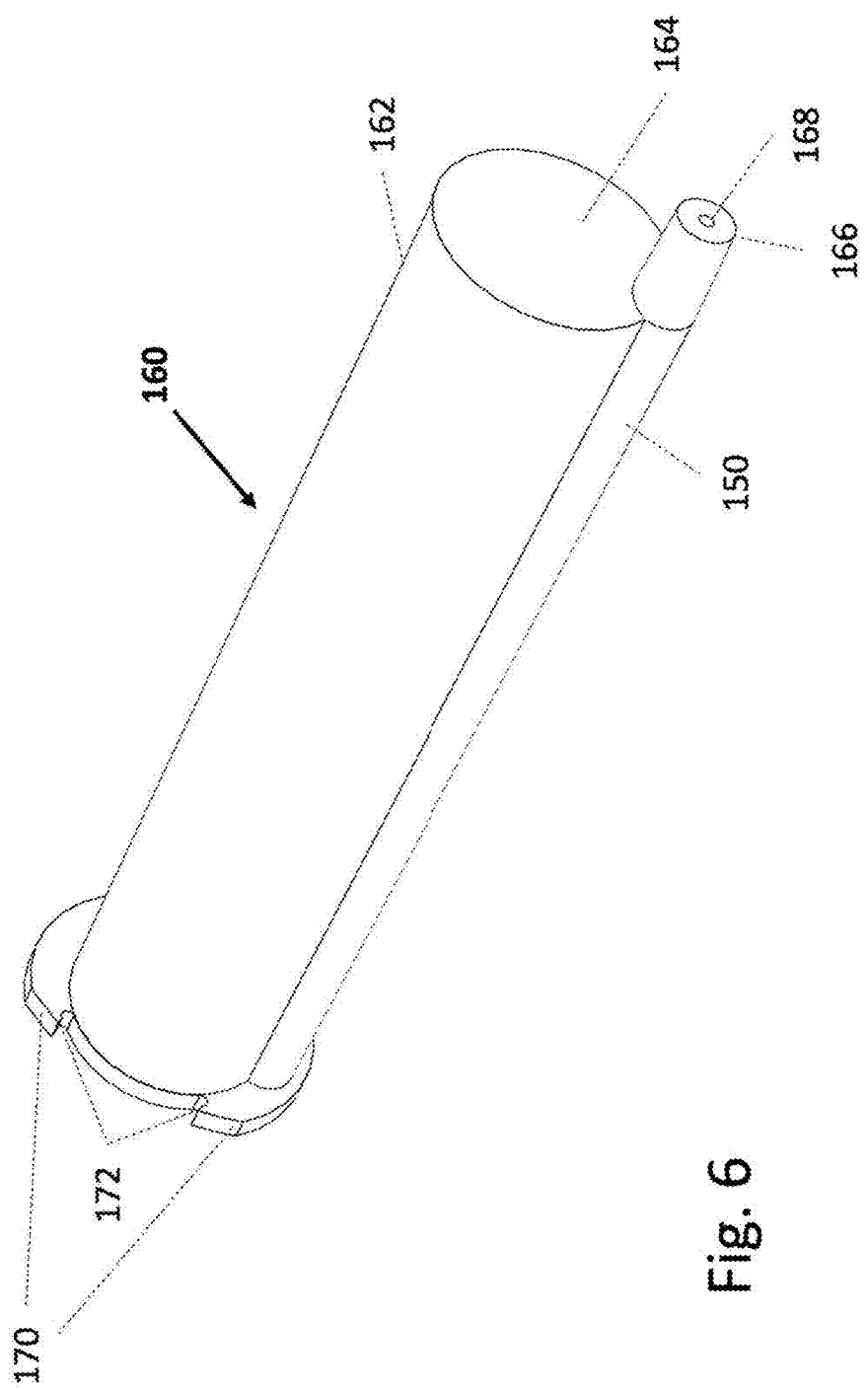
FIG. 6 is a perspective view of a barrel of the syringe of FIG. 1.
Figure 7:
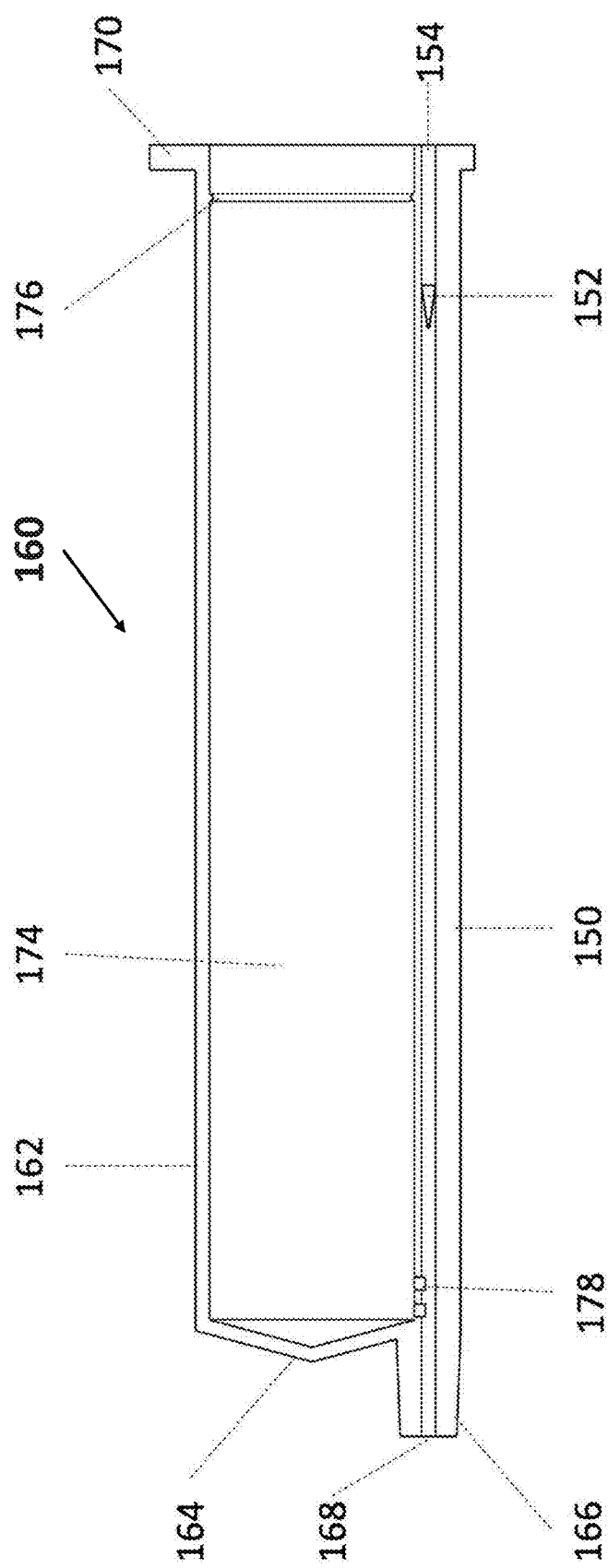
FIG. 7 is a cross-sectional view of the barrel of FIG. 6 along a central longitudinal axis.
Figure 8:
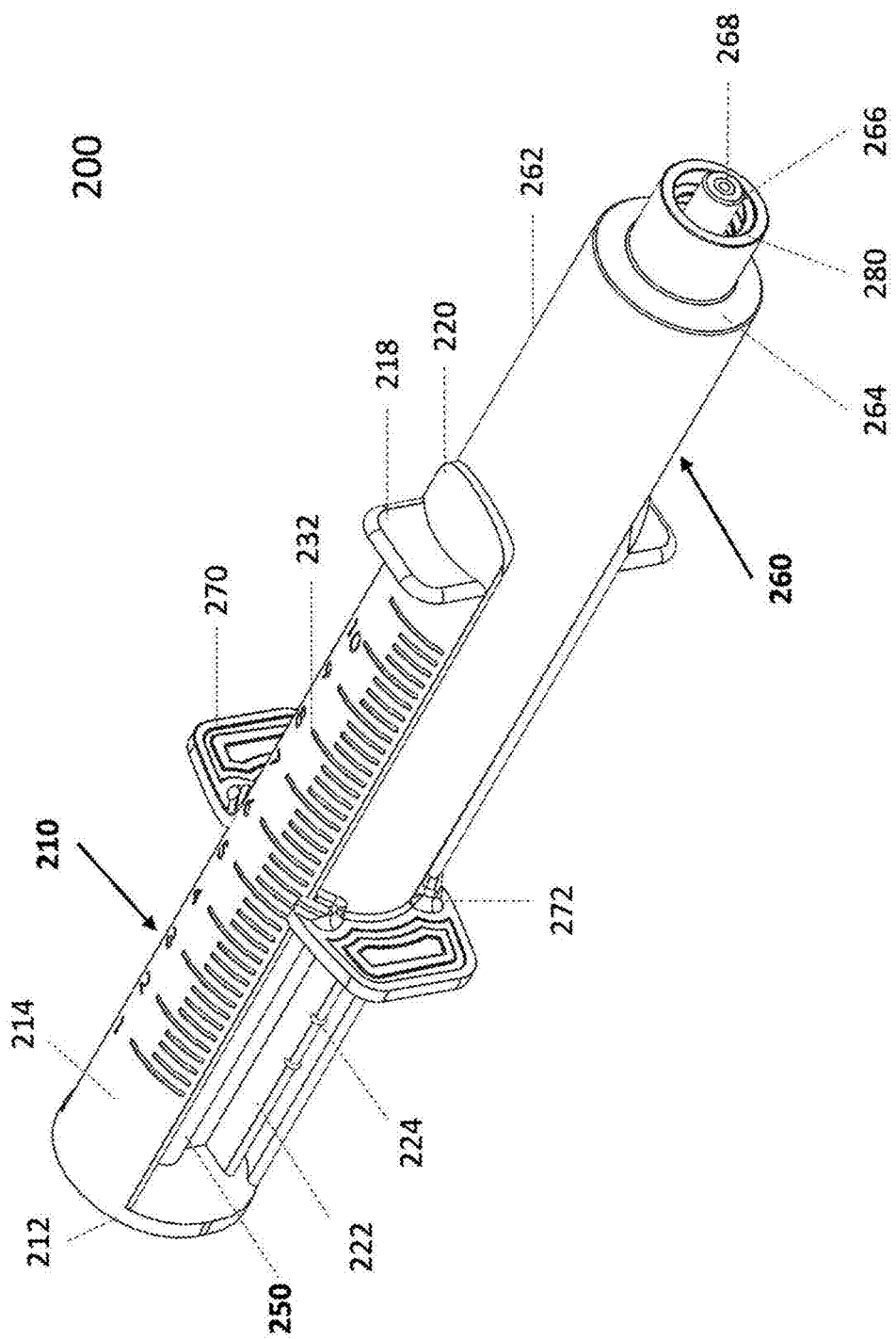
FIG. 8 is a perspective view of a syringe with an adapter for single-handed use of the syringe and including a guidewire tract according to a second embodiment.
Figure 9:
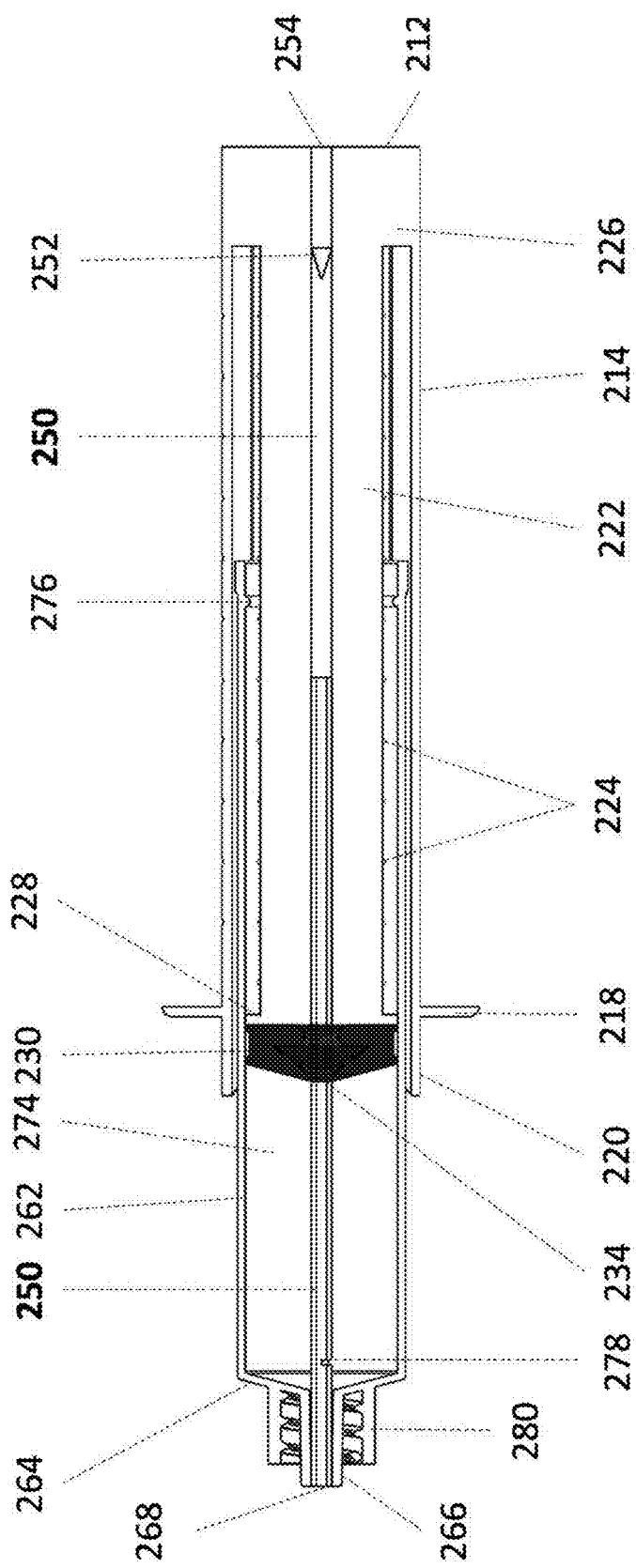
FIG. 9 is a cross-sectional view of the syringe shown in FIG. 8 along a central longitudinal axis.
Figure 10:
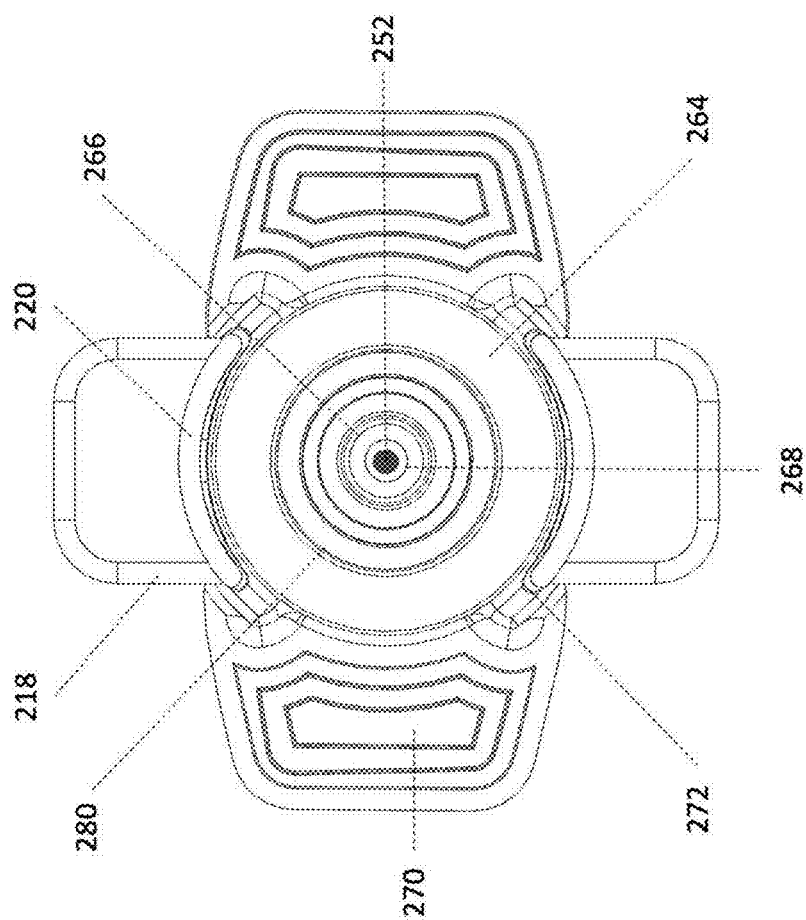
FIG. 10 is a front view of the syringe shown in FIG. 8 along a central longitudinal axis.
Figure 11:
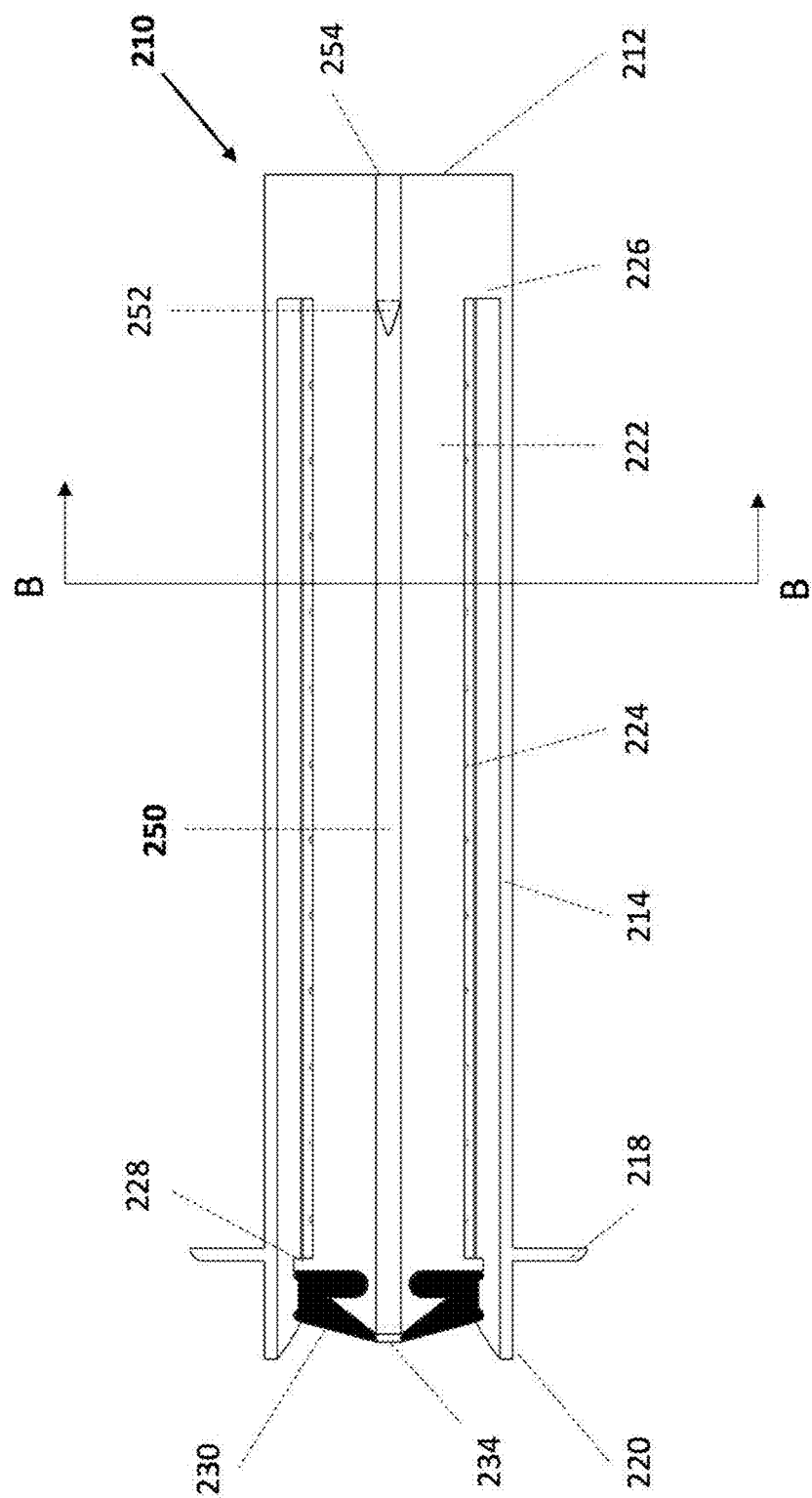
FIG. 11 is a cross-sectional view of the plunger shown in FIG. 8 along a central longitudinal axis.
Figure 12:
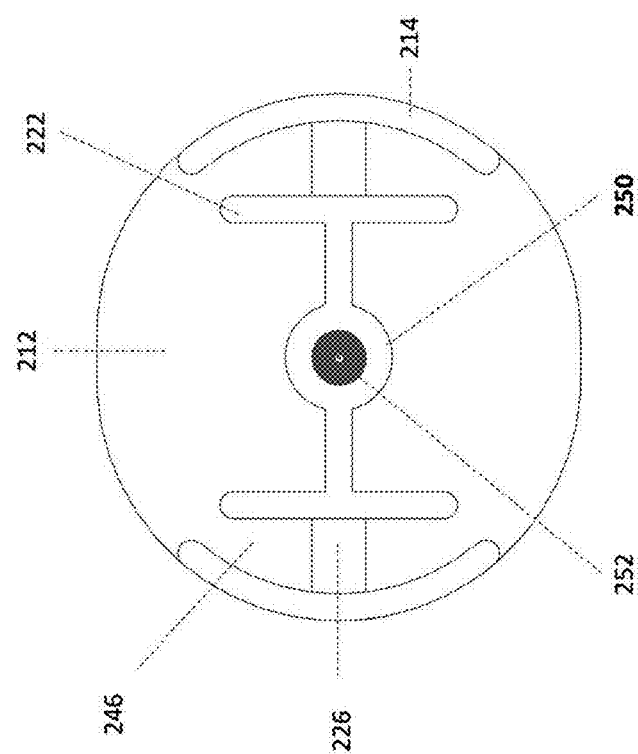
FIG. 12 is a cross-sectional view along B-B of the plunger of FIG. 11.
Figure 13:
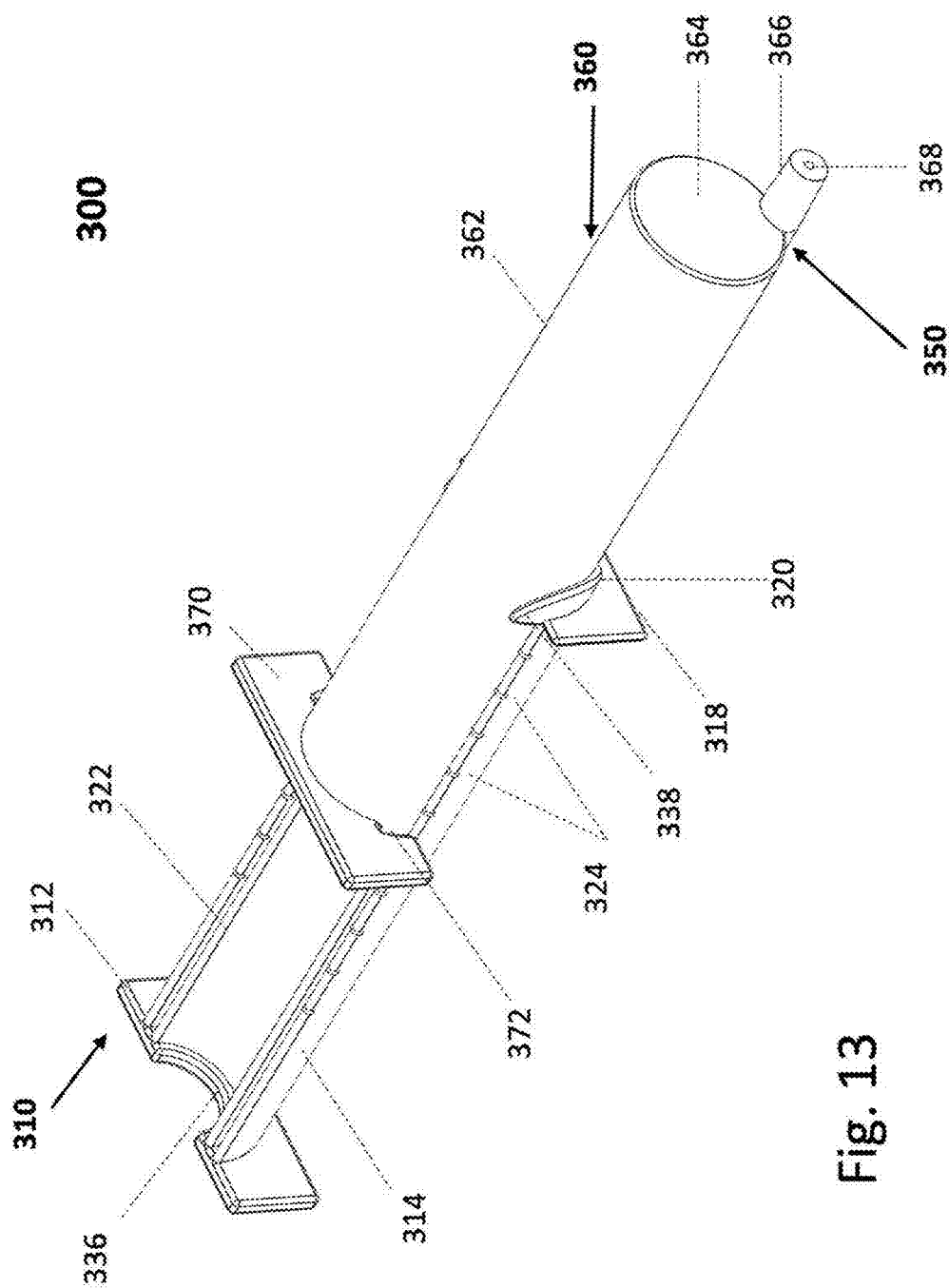
FIG. 13 is a perspective view of a syringe with an adapter for single-handed use of the syringe and including a guidewire tract according to a third embodiment.
Figure 14:
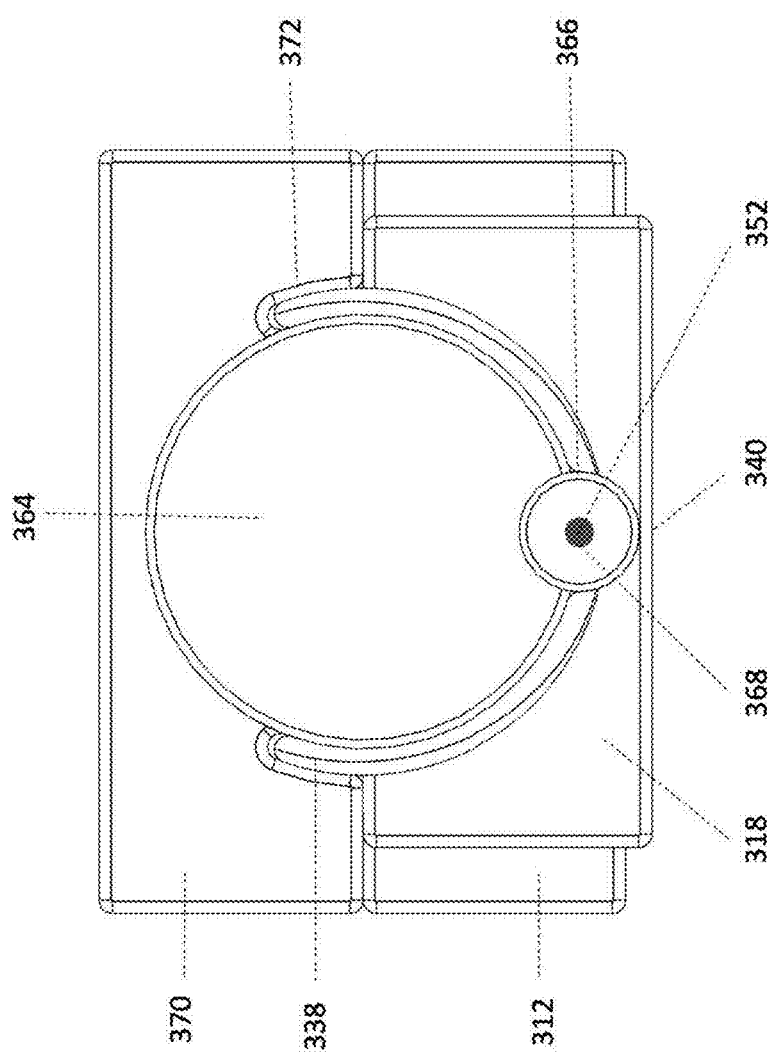
FIG. 14 is a front view of the syringe shown in FIG. 13 along a central longitudinal axis.
Figure 15:
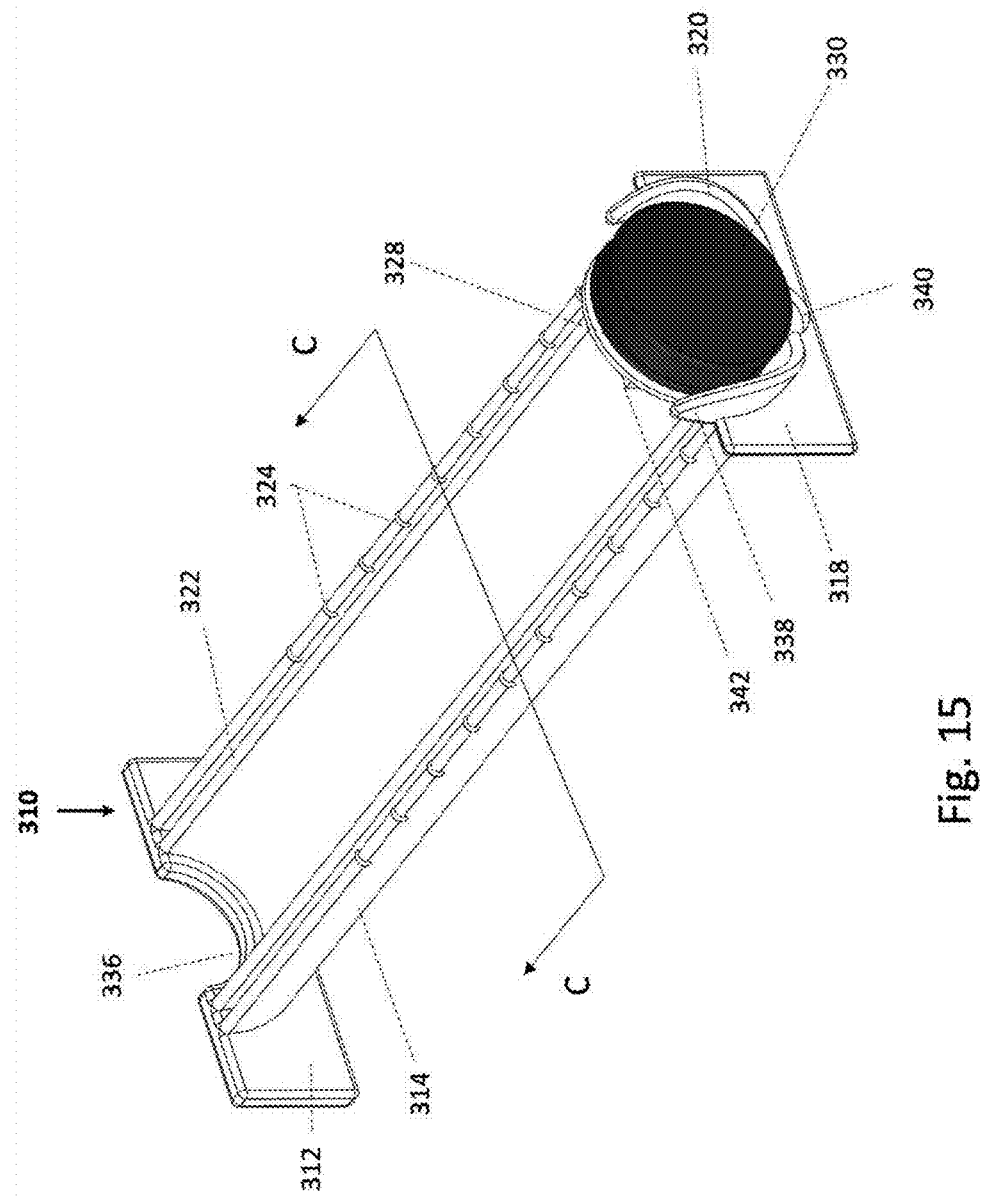
FIG. 15 is a perspective view of the plunger of FIG. 13.
Figure 16:
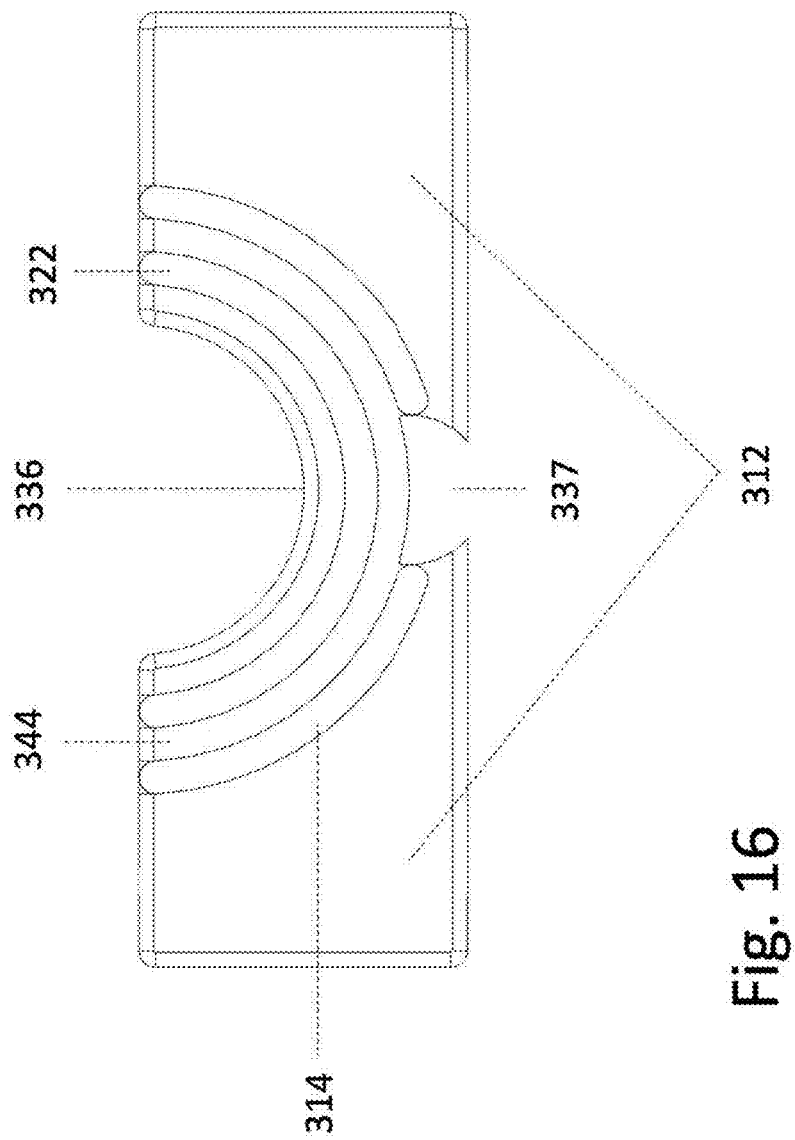
FIG. 16 is a cross-sectional view along C-C of the plunger of FIG. 15.
Figure 17:
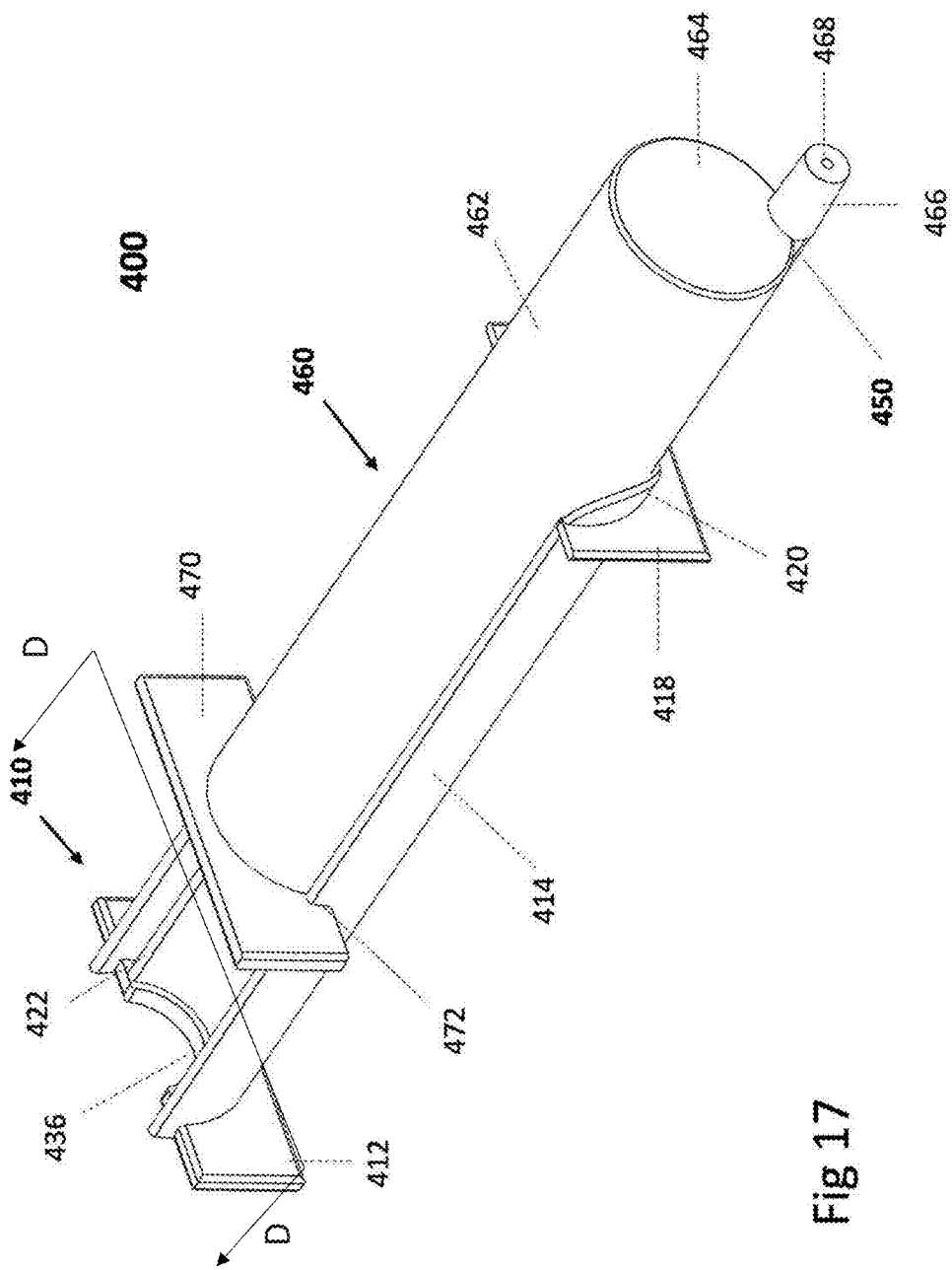
FIG. 17 is a perspective view of a syringe with an adapter for single-handed use of the syringe and including a guidewire tract according to a fourth embodiment.

The barrel 160 will now be described in detail with reference to FIGS. 6 and 7. The barrel 160 includes the barrel body 162 that, with the front end 164, define the syringe cavity 174. The barrel body 160 has a generally cylindrical main body is hollow and tapered to the front end 164. The front end 164 of the barrel body 162 may have any shape, e.g., conical, curved, flat, etc., to match a front surface of the seal 130 of the plunger 110. The arcuate shape of the inner surface of the external arm 114 matches and abuts an outer surface of the barrel body 162 and the arcuate shape of the outer surface of the internal arm 122 matches and abuts an inner surface of the barrel body 162, such that the barrel body 162 is sandwiched between the external arms 114 and internal arms 122 on opposite sides thereof.

A rear end of the barrel 160 may include second flanges 170, e.g., rearward flanges or barrel flanges, having an external arm passage 172. The external arm passage 172 allows the barrel body 162 to be inserted between the external arms 114 and the internal arms 122, while straightening the movement of the plunger 110 and minimizing external arm 114 deviation away from the barrel body 162. In particular, the external arm passage 172 is large enough to allow the first flanges 118 to pass therethrough unimpeded, while allowing the second flange 170 to partially overlap the external arm 114 along the first direction. The second flanges 170 may extend radially outward along a second direction, orthogonal to the longitudinal direction of the syringe and to the first direction the plunger flanges 118 of the plunger 110. While the second flange 170 is illustrated as being part of the barrel 160, the second flange may be separate from the barrel 160. The second flanges 170 may be used for control of aspiration or injection.

In other words, the pair of external arms 114 and internal arms 122 do not completely surround the barrel body 162, facilitating the simple arrangement of first flanges 118 and second flanges 170 that do not interfere with the first flanges 118, while the external arm passage allows the second flanges 170 to partially overlap the external arm 114, such that movement of the plunger 110 is stably facilitated.

The barrel 160 includes an internal prominence 176, e.g., a circular prominence, in an inner surface of a rear side on the barrel body 162. The internal prominence 176 gives tactile feeling when the nubs 124 contact it and stops the plunger 110 when the seal 130 of the plunger 110 contacts it, such that accidental complete removal of the plunger 110 may be prevented.

The guidewire tract 150 may be integral with the barrel body 162 and may extend along one side thereof between the pair of arms of the plunger 110 in parallel with a central longitudinal axis of the syringe barrel 160, i.e., is offset form the central longitudinal axis of the syringe barrel 160. A nozzle 166 to which a needle or a tube is to be affixed may be provided at an anterior end of the guidewire tract. The nozzle 166 may overlap, e.g., completely overlap, the guidewire tract along the longitudinal direction and may overlap, e.g., partially overlap, the front portion 164 of the barrel body 162 along the longitudinal direction. The barrel 160 includes barrel front openings 178 that are small openings to establish fluid communication between a nozzle 166 and the syringe cavity 174. Using a minimum number and a minimum size of front openings 178 that are sufficient to allow for fluid communication may help maintain the integrity and strength of the guidewire tract 150. The nozzle 166 may extend further along the longitudinal direction than the front end 164. A nozzle lumen 168 is the hollow bore that allows fluid to and from the syringe cavity 174 to flow therethrough.

The guidewire tract 150 may overlap and share the nozzle lumen 168, such that the central hollow region or tunnel that is continuous through the guidewire tract 150 and the nozzle lumen 168. The guidewire tract 150 may include a guidewire tract rear opening 154 that allows a guidewire to be inserted therein and a guidewire tract valve 152. The guidewire tract valve 152 allows the guidewire to pass therethrough, while preventing the sample in the syringe cavity 174 from leaking out of the syringe 100 through the guidewire tract 150 lumen and preventing gas from entering the syringe cavity 174 as well. The guidewire tract valve 152 may be closer to the guidewire tract rear opening 154 than to the nozzle 166.

The syringe seal 130 is attached to a front end of the plunger 110 and is inserted into the syringe cavity 174; i.e. the opening of the barrel 160. The syringe seal 130 fits to the inner wall of the barrel body 162 and has a front surface that corresponds to an inner surface of the front end 164. Thus, when the plunger 110 is pressed on the push button 112 toward the front end 164 of the barrel body, fluid in the syringe cavity 174 between the syringe seal 130 and the nozzle 166 is urged toward the nozzle 166 and emitted through the front opening 178 of the barrel 160 toward the nozzle lumen 168. If a needle is affixed to the nozzle 166, the sample is ejected from the needle. During an aspiration operation, the plunger 110 is drawn away from the nozzle 166 so that a vacuum is created, and sample (air, gas, or a liquid) that is adjacent to the nozzle lumen 168 is drawn into the syringe cavity 174 through the front opening 178 of the barrel 160. The syringe parts may be made from plastic, such as polypropylene for the barrel 160, and polyethene for the plunger 110. While the present embodiment uses parts made from plastic and synthetic rubber, other materials may be used as well, e.g., glass and stainless steel barrels and/or plungers.

During an aspiration operation, the first flanges 118 and the second flanges 170 are used by the user. To aspirate, an operator places one or more fingers, e.g., index and middle fingers, on a forward surface of the first flange 118 and a thumb on a rear surface of second flanges 170. When the operator pinches thumb and other fingers together, the pinching force urges the plunger 110 backwards, and thus withdraws the plunger 110 from the body 162 of the barrel 160, thus aspirating the sample inside the syringe cavity 174 through barrel front openings 178. In large sized syringes, an additional flange is added on the middle of the external arm 114, the aspiration will start when operator places one or more fingers, e.g., index and middle fingers, on a forward surface of plunger's additional flange and a thumb on a rear surface of second flanges 170. When the operator pinches thumb and other fingers together, the pinching force urges the plunger 110 backwards to its midway, further backward movement will happen when operator moves his fingers to be on a forward surface of first flange 118 and pinches thumb and other fingers together again, the pinching force urges the plunger 110 backwards to the end, and thus withdraws the plunger 110 from the body 162 of the barrel 160, thus aspirating the sample completely inside the syringe cavity 174 through barrel front openings 178.

During an injection operation, the operator places one or more fingers, e.g., index and middle fingers, over a forward surface of the second flange 170 and a thumb on the push button 112. The operator's index and middle fingers are placed directly on the second flange 170 so the fingers do not contact the external arms 114 of the plunger 110, which will slide forward as a result of the force exerted by pinching thumb and fingers together, which in turn pushes the plunger 110 forward without the operator's fingers interfering with the movement of the plunger 110. In large sized syringes, with an additional flange is added on the middle of the external arm 114, the injection will start when the operator places one or more fingers, e.g., index and middle fingers, over a forward surface of the second flange 170 and a thumb on the rear surface of additional flange which will slide forward as a result of the force exerted by pinching thumb and fingers together, which in turn pushes the plunger 110 forward to its midway, and to complete the injection, the operator moves a thumb to be on the push button 112 while the fingers e.g., index and middle fingers, are still over a forward surface of the second flange 170, by pinching thumb and fingers together the plunger 110 will slide forward.

In addition to allowing the operator to use one hand to operate the syringe 100 for aspiration/injection, the syringe 100 described above allows a guidewire to be passed through the guidewire tract 150 and the nozzle 166 for precise and easy handling with another hand of the operator.

FIGS. 8-12 illustrate a syringe 200 for single-handed injection/aspiration operation with an integrated guidewire tract according to a second embodiment. The syringe 200 includes a plunger 210, a barrel 260, and a guidewire tract 250. The parts of the syringe are the same as the parts of the first embodiment, first flanges 118/218, introducer 120/220, nubs 124/224, arms connector 126/226, arms gap 146/246, guidewire tract valve 152/252, barrel body 162/262, nozzle 166/266, nozzle lumen 168/268 and circular prominence 176/276 are the same as the first embodiment so explanations of these components are provided above, or kept to a minimum in the present explanation.

In the second embodiment, the guidewire tract 250 is formed coaxially with the central axis of the syringe 200. In particular, the guidewire tract 250 includes two portions, a plunger guidewire tract 256 and a barrel guidewire tract 258. The plunger guide wire tract 256 includes a guidewire tract rear opening 254, i.e., a push button 212 of the plunger 210 includes an opening 254, e.g., a circular opening, to allow access to the guidewire tract rear opening 254, and a guidewire tract valve 252. The plunger guidewire tract 256 has an inner surface that is friction fit to an outer surface of the barrel guidewire tract 258 to allow the plunger 210 to move readily in the barrel 260 while allowing the guidewire to pass therethrough. The plunger guidewire tract 256 and the barrel guidewire tract 258 may be made of different materials, e.g., the plunger guidewire tract 256 may be plastic and the barrel guidewire tract 258 may be metal.

An outer surface of an external arm 214 of the plunger 210 may include a visual scale 232, e.g., with luminescent indicia that are visible in the dark, to provide a visual complement to the tactile feedback provided by the nubs 224 regarding the movement of the plunger 210 within the syringe barrel 260. The scale 232 includes numbers arranged from higher to lower digits from front to rear. The plunger 210 includes a seal 230 that includes a plunger front opening 234 to allow the plunger guidewire tract 256 to pass therethrough. Additional flanges can be added over the outer surface of the external arms.

The barrel 260 includes second flanges 270 and external arm passages 272 that allow the introducer 220 and the external arm 214 of the plunger 210 to pass in and out relative to the barrel 260. The barrel 260 includes a barrel front opening 278 that are small openings on one side of front end of barrel guidewire tract 258 to establish fluid communication between a nozzle lumen 268 and the syringe cavity 274. The barrel front opening 278 may only be in one side of the barrel 260 as more openings and/or larger openings may weaken the barrel guidewire tract 258. The nozzle 266 may extend further along the longitudinal direction and protrude from a front end 264 of the body 262. A Luer lock 280 may be provided to secure tubes or needle connections to the nozzle 266.

Internal arms 222 may be connected to each other by a stopper 228 at the front end of the plunger 210. The stopper 228 prevents the plunger 210 from falling out as the stopper will stop when it contacts the internal prominence 276 of the barrel 260. Unlike in the previous embodiment, in which the stopper 128 is on the external arms 114, the stopper 228 is on the internal arms 222. Further, as may be seen in FIG. 12, unlike the previous embodiment, the internal arms 214 may not be arcuate, e.g., may have a straight cross-section. A syringe seal 230 is on the stopper 228 and seals the air going inside or fluid going outside the syringe cavity 274.

FIGS. 13-16 illustrate a syringe 300 for single-handed injection/aspiration operation with an integrated guidewire tract according to a third embodiment. The syringe 300 includes a plunger 310, a barrel 360, and a guidewire tract 350. The parts of the syringe 300 that are the same as the parts of the first embodiment include, guidewire tract 150/350, guidewire tract valve 152/352, guidewire tract rear opening 154/354, barrel body 162/362, front end 164/364, nozzle 166/366, nozzle lumen 168/368, syringe cavity 174/374, circular prominence 176/376, and barrel front opening 178/378 are the same as the first embodiment so explanations of these components are provided above, or kept to a minimum in the present explanation. Further, parts of the syringe 300 that are the same as the parts of the second embodiment include stopper 228/328.

The plunger 310 includes arcuate external arms 314 and a single, continuous arcuate internal arm 322 defining an arms gap 346 in contrast to the pair of inner arms in the previous embodiments. The external arms 314 and the internal arm 322 are in the shape of cylindrical segment, e.g., half of a cylinder. The arms gap 346 (see FIG. 16) between the external arms and the internal arm is sufficient to accommodate a barrel body 362 of the barrel 360. A guidewire tract gap 337 is between the medial ends of external arms 314 to allow the guidewire tract 350 to pass between them. Here, instead of being on the internal arm 322, each external arm 314 may include nubs 324 protruding from an outer surface thereof to provide tactile sensation and feedback when the plunger 310 moves in and out of a syringe cavity 374, e.g., depressing/retracting the plunger 310.

The first flange 318 is a continuous generally rectangular flange 318 on a lower surface of the external arm 314 with a first flange connector 340 that prevents the external arms 314 from deviating away (laterally) of barrel body 362, a gap 337 between the external arms 314, as compared with a pair of opposing flanges in the previous embodiments, with an extended lower portion that allows the guidewire tract 350 to pass therethrough. Of course, the first flange 318 may be any shape that provides sufficient support for an operator to operate the syringe 300 as long as the barrel 360 and the guidewire tract 350 are accommodated.

At the front end, the plunger 310 includes an external arm holder 338. The external arm holder 338 are crescentic prominences extending forward from the external arm 314, partially surrounding the barrel body 362, but further than the external arm 314. The external arm holder 338 holds the external arms and prevents the external arm 314 from giving way downward, e.g., while aspirating. The external arm holder may overlap the introducer 320.

At the rear end, the plunger 310 includes a push button 312, e.g., a generally rectangular push button 312 including an opening 344, e.g., an arcuate or hemispherical opening, in an upper surface thereof and having a rear groove 336, e.g., an arcuate rear groove, on an upper, inner surface thereof extending along the internal arm 322. The rear grove 336 is a semicircular groove on the inner side of push button 312 to decrease a chance of finger friction to push button 312, e.g., while aspirating when plunger 310 is fully inside the barrel 360. A guidewire tract gap 337 between the medial ends of external arms 314 to allow the guidewire tract 350 to pass between them. Of course, the push button 312 may have any shape that provides sufficient support for an operator to operate the syringe 300 as long as the barrel 360 and the guidewire tract 350 are accommodated.

The barrel 360 is substantially the same as the barrel 160, except for the second flanges 370. In this embodiment, a single, continuous generally rectangular second flange 370 is provided on a side opposite the first flange 318, e.g., on an upper surface of the barrel body 362, and having, in a lower surface, an arcuate opening 372 corresponding to the barrel body 362 and an external arm passage on either side thereof. The external arm passage 372 allows the external arm holder 338 to pass therethrough. Of course, the second flange 370 may be any shape that provides sufficient support for an operator to operate the syringe 300 as long as the plunger 310 is accommodated.

FIGS. 17-22 illustrate a syringe 400 for single-handed injection/aspiration operation with an integrated guidewire tract according to a fourth embodiment. The syringe 400 includes a plunger 410, a barrel 460, and an offset guidewire tract 450. The parts of the syringe 400 that are the same as the parts of the first and third embodiments include, seal 130/330/430, guidewire tract gap 337/437, first flange connector 340/440, guidewire tract 150/350/450, guidewire tract valve 152/352/452, guidewire tract rear opening 154/354/454, barrel body 162/362/462, front end 164/364/464, nozzle 166/366/466, nozzle lumen 168/368/468, syringe cavity 174/374/474, circular prominence 176/376/476, and barrel front opening 178/378/478, so explanations of these components are provided above, or kept to a minimum in the present explanation. Further, parts of the syringe 400 that are the same as the parts of the third embodiments include, stopper 328/428, seal support 342/442, first flange 318/418, internal arm 322/422, nubs 324/424, opening 344/444, and arms gap 346/446 so explanations of these components are provided above, or kept to a minimum in the present explanation.

The plunger 410 has an external arm 414 that extends further upwards than the internal arm 422. For example, the external arm 414 may be coextensive with the external arm holder 338 of the third embodiment.

Figure 18:
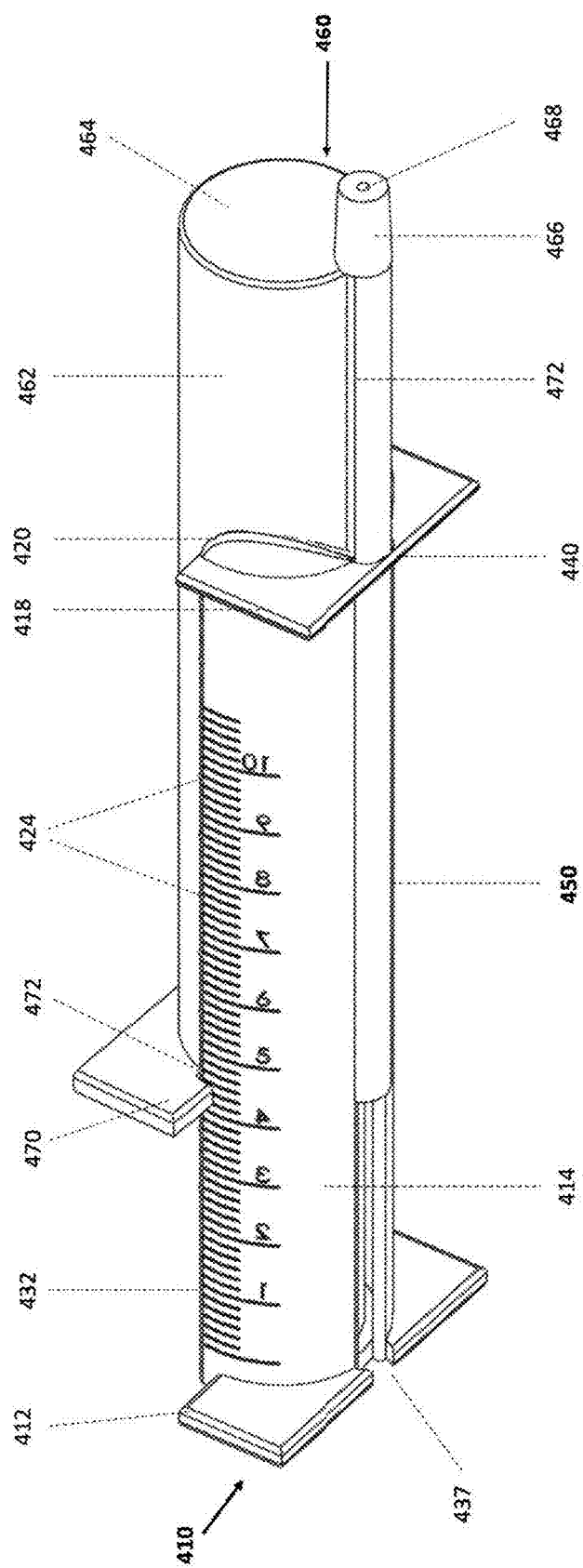
FIG. 18 is another perspective view of a syringe showing the scale over the outer surface of external arms of FIG. 17.

In another modification, shown in FIG. 18 a scale 432 may be provided on the plunger 410.

Figure 19:
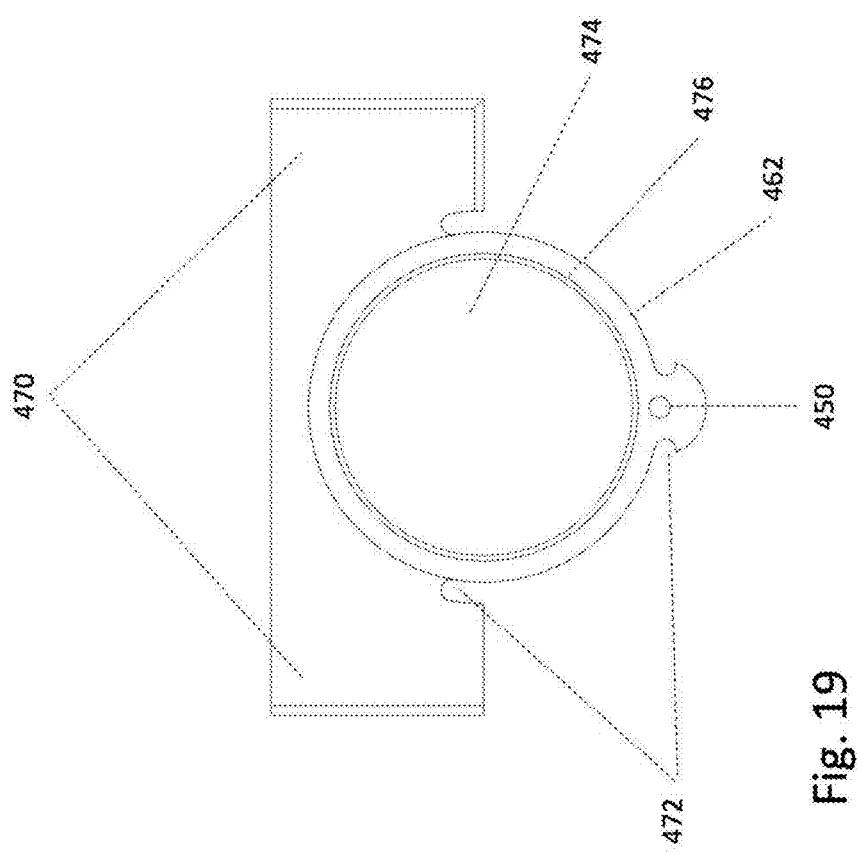
FIG. 19 is cross-sectional view along D-D of the barrel shown in FIG. 17.

The barrel 460 is substantially the same as the barrel 160/360, except for the second flanges 470 which almost similar to the flanges of previous embodiment. For example, since the external arm 414 now extends through the first flange 418 and serves as an introducer 420, the barrel 460 includes a pair of external arm passages 472 that allows the external arm 414 to pass therethrough and provides mechanical support as shown in FIG. 19. In particular, in addition to an external arm passage 472 in a second flange 470, a portion of the body 462 adjacent to the guidewire tract 450 also includes an external arm passage 472.

Figure 20:
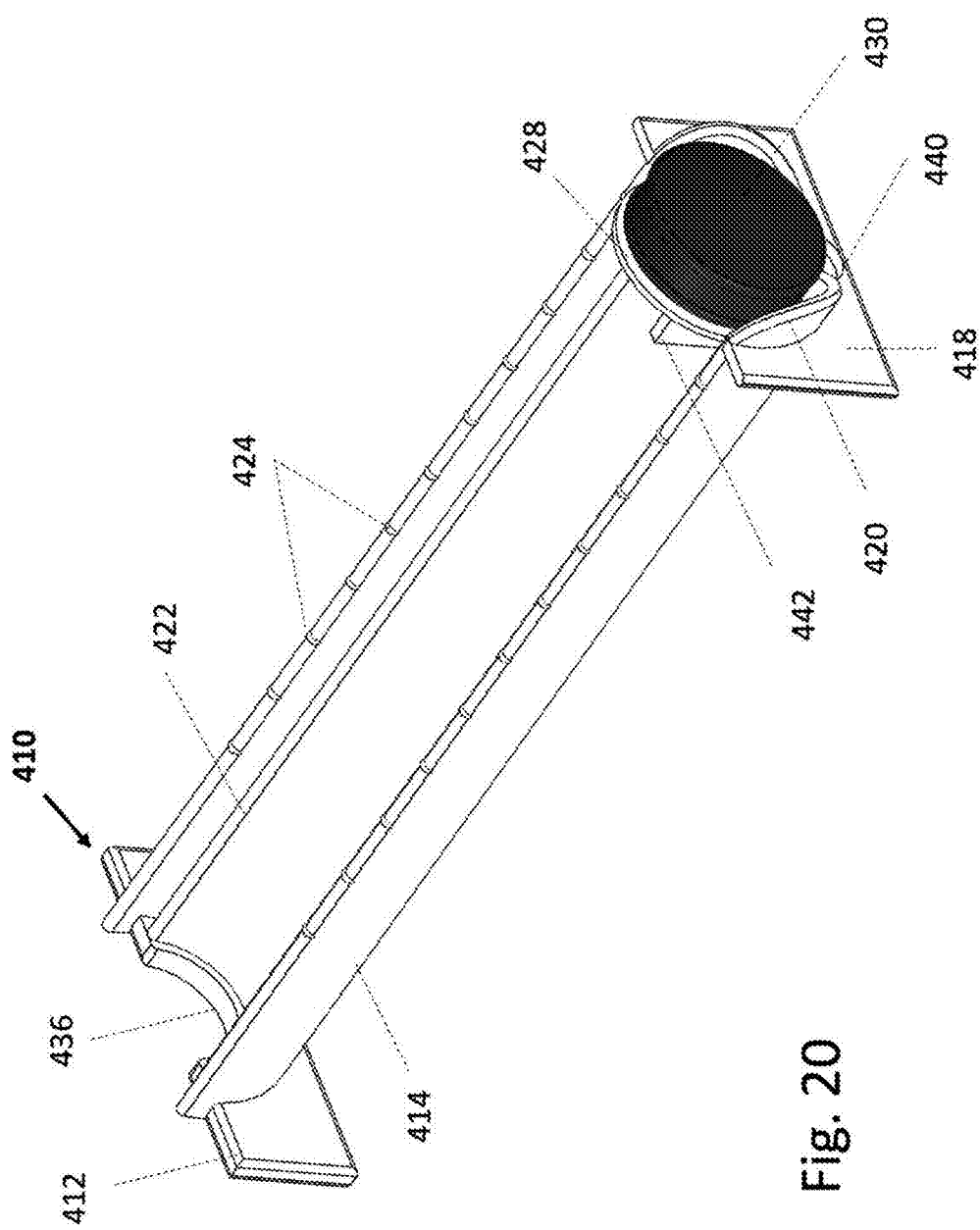
FIG. 20 is a perspective view of the plunger of FIG. 18.
Figure 21:
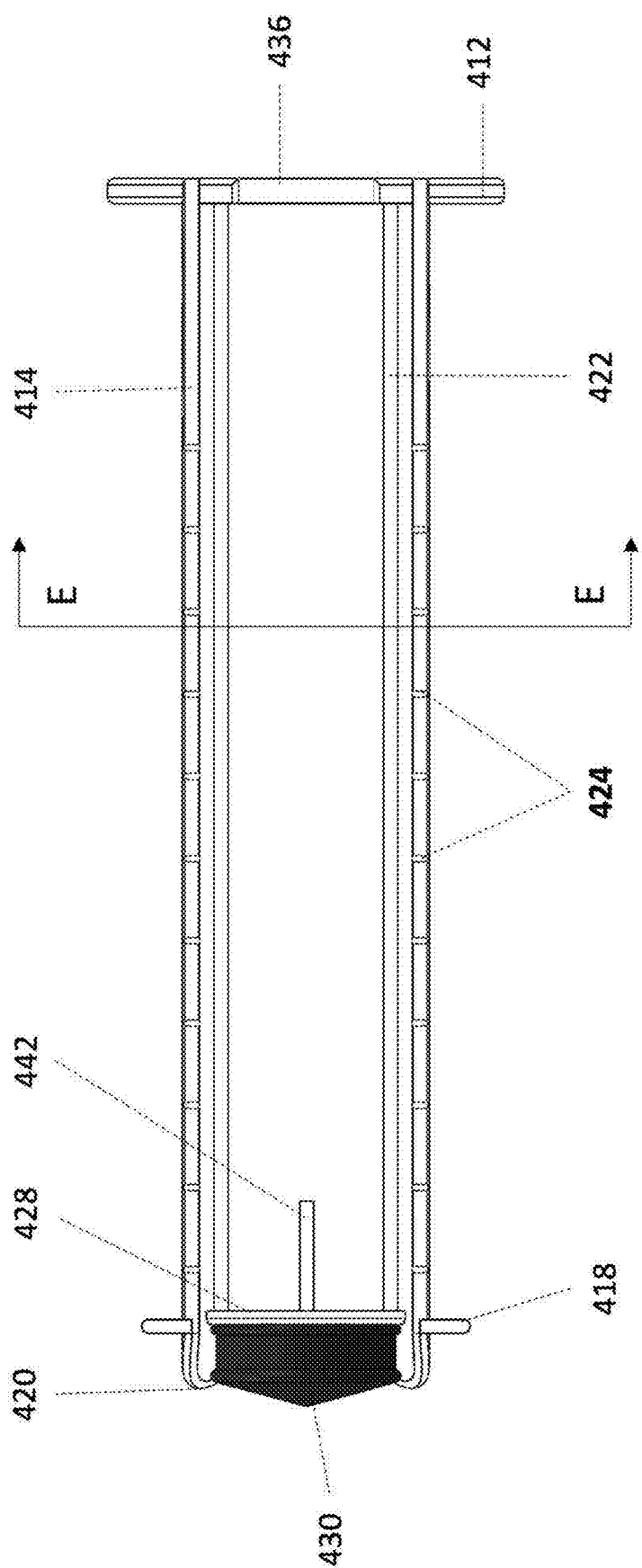
FIG. 21 is a side longitudinal view of the plunger shown in FIG. 20.
Figure 22:
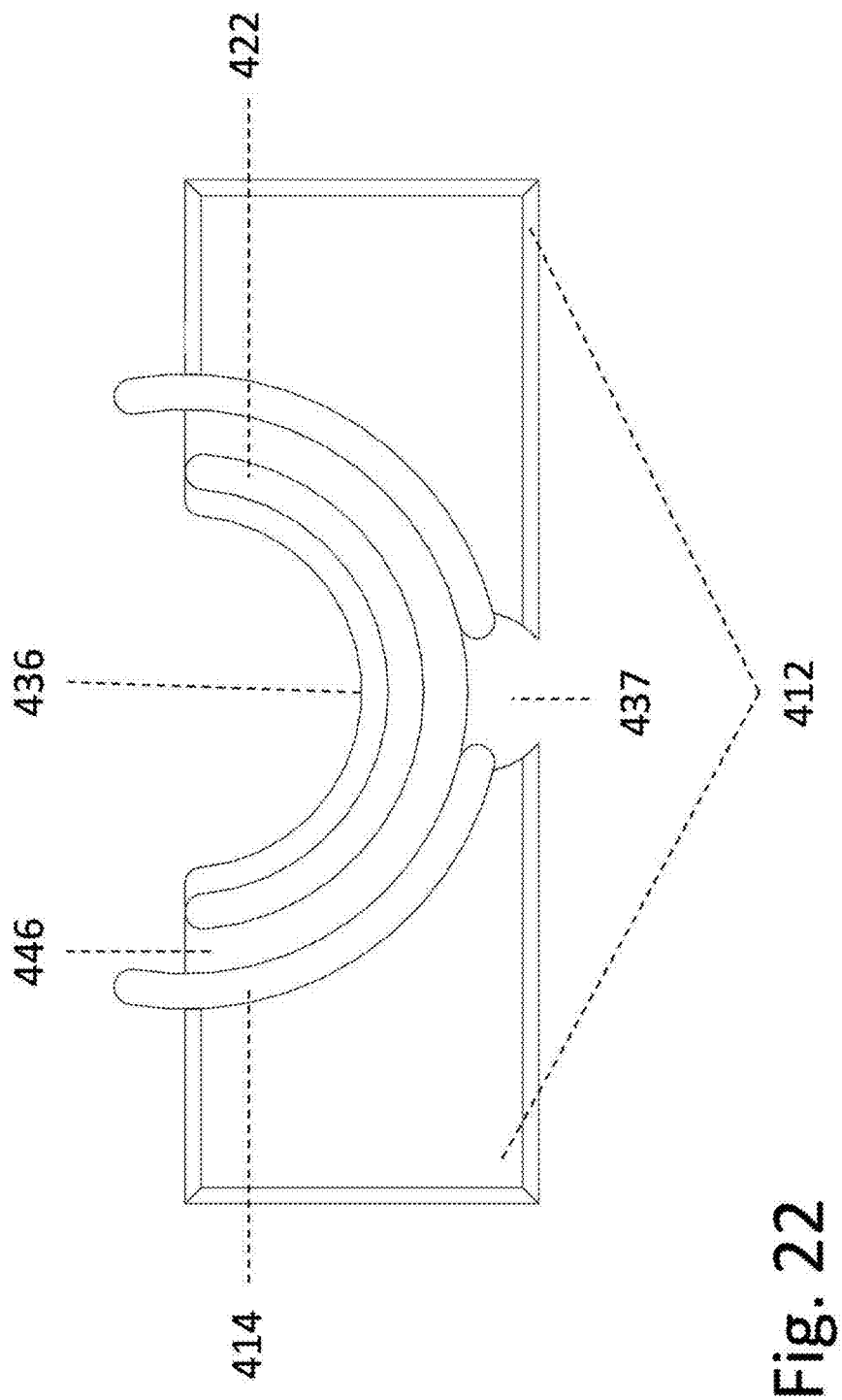
FIG. 22 is a cross-sectional view along E-E of the plunger of FIG. 21.

In a modification shown in FIGS. 20-21, the external arms 414 may include nubs 424 and the plunger 410 may include at least one seal support 442. The seal support 442 provide mechanical reinforcement to the seal 420 to decrease bending of the seal 420 during aspiration or injection. The seal support may have different shapes, lengths, sizes, etc., depending upon the type and size of the syringe.

Various embodiments are described herein are brief summaries of selected embodiments are shown below.

(1) According to an embodiment, a hand-held syringe configured for integrated aspiration and guidewire operations, includes:

a plunger having
a seal at a forward end thereof,
a plunger push button at a rear end thereof,
an internal plunger arm attached at a rear end thereof to the plunger push button and to the seal at a forward end thereof, and
an external plunger arm attached at a rear end thereof to the plunger push button, the internal plunger arm being arranged co-axially with the external plunger arm and separated by a gap;
a first flange that extends radially away from the external plunger arm at the forward end thereof;
a barrel having
a wall having a thickness that is accommodated by the gap, at least a portion of the wall being disposed in the gap between the internal plunger arm and external plunger arm, and
a nozzle at a forward end thereof;
a second flange that extends radially away from the barrel at a rear end thereof; and
a guidewire tract integrated with at least one of the plunger and the barrel.

(2) The syringe of (1) wherein the guidewire tract is integral with the barrel and offset from a central longitudinal axis of the barrel.

(3) The syringe of any of (1) and (2), further including at least a front opening between the guidewire tract and the forward end of the barrel that allow fluid communication between a syringe cavity and a tunnel of guidewire tract.

(4) The syringe of any of (1) to (3), further including a guidewire tract valve rear to the barrel front opening.

(5) The syringe of any of (1) to (4), wherein the second flange covers the guidewire tract.

(6) The syringe of any of (1) to (5), wherein the plunger push button includes an opening for the guidewire tract.

(7) The syringe of any of (1) to (6), wherein the first flange includes a gap for the guidewire tract.

(8) The syringe of any of (1) to (7), wherein the nozzle overlaps the guidewire tract and extending beyond a forward end of the barrel, the nozzle including a nozzle lumen that, with the guidewire tract, forms a continuous tunnel along the syringe.

(9) The syringe of any of (1) to (8), wherein the guidewire tract is integral with the plunger and the barrel and is coaxial with a central longitudinal axis of the plunger and the barrel.

(10) The syringe of (9), wherein the guidewire tract includes a plunger guidewire tract and a barrel guidewire tract that form a continuous tunnel along the syringe.

(11) The syringe of (10), further comprising a guidewire tract valve in the plunger guidewire tract front to the rear opening of guidewire tract.

(12) The syringe of (10), further including an opening in the seal to allow the plunger guidewire tract and the barrel guidewire tract to extend therethrough.

(13) The syringe of any of (1) to (13), wherein the second flange partially overlaps the external plunger arm and includes an external arm passage that allows the external plunger arm to pass therethrough.

(14) The syringe of claim (13), wherein the external plunger arm extends further upward along the barrel than the internal plunger arm and the external arm passage provides a groove that allows the external plunger arm to pass therethrough.

(15) The syringe of any of (1) to (14), wherein the external plunger arm includes an introducer that extends forward past the first flange.

(16) The syringe of any of (1) to (15), wherein the plunger includes a pair of external plunger arms and a pair of internal plunger arms, on opposing sides of a central longitudinal axis of the syringe, each pair attached at a rear thereof to the plunger push button and providing the gap.

(17) The syringe of (16), wherein the first flange includes at least a pair of front flanges, each flange extending radially outwards from a corresponding external plunger arm in a first direction.

(18) The syringe of (17), wherein the second flange includes a pair of second flanges, each second flange extending radially outwards from the barrel wall between the pair of external plunger arms in a second direction orthogonal to the first direction.

(19) The syringe of any of (16) to (18), wherein each external plunger arm includes a spine protruding therefrom along a central longitudinal direction thereof.

(20) The syringe of any of (1) to (19), wherein the external plunger arm and the internal plunger arm are arcuate.

(21) The syringe of any of (1) to (20), wherein the external plunger arm and the internal plunger arm have a connector between them at their rear end.

(22) The syringe of any of (1) to (21), wherein at least one of the external plunger arm and the internal plunger arm have nubs thereon.

(23) The syringe of any of (1) to (22), wherein the plunger push button has an opening corresponding to the internal plunger arm in an inner surface thereof.

(24) The syringe of any of (1) to (23), wherein the plunger push button includes a gap to allow the guidewire tract therethrough and a groove on an upper inner surface.

(25) The syringe of any of (1) to (24), wherein the first flange on the external plunger arms have a gap between thereof and that allows the guidewire tract therethrough.

(26) The syringe of (25), wherein the gap has a width corresponding to guidewire tract external wall.

(27) The syringe of any of (25) and (26), wherein the second flange is corresponding to the wall in a lower surface thereof and an external arm passage on either side of the gap that allows the external plunger arm therethrough.

(28) The syringe of any of (1) to (27), further including a scale having luminescent indicia on the plunger external arm.

(29) The syringe of any of (1) to (28), further including a seal support extending from a rear surface of the seal towards the plunger push button.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Obviously, numerous modifications and variations of the present invention are possible in light of the above teachings. It is therefore to be understood that within the scope of the appended claims, the invention may be practiced otherwise than as specifically described herein.

DRAWING ELEMENTS 100, 200, 300, 400: Syringe for singlehanded operation including a guidewire tract
110, 210, 310, 410: Plunger
112, 212, 321, 412: Push Button
114, 214, 314, 414: External Arm
116: External Arm Spine
118, 218, 318, 418: First Flanges
120, 220, 320, 420: Introducer
122, 222, 322, 422: Internal Arm
124, 224, 324, 424: Nubs
126, 226, 326, 426: Arms Connector
128, 228, 328, 428: Stopper
130, 230, 330, 430: Seal
232, 432: Scale
234: Plunger Front Opening
336, 436: Rear Groove
337, 437: Guidewire Tract Gap
338: External Arm Holder
340, 440: First Flange Connector
342, 442: Seal Support
144: Push Button Opening
146, 246, 346, 446: Arms Gap
150, 250, 350, 450: Guidewire tract
152, 252, 352, 452: Guidewire Tract Valve
154, 254, 354, 454: Guidewire tract Rear Opening
160, 260, 360, 460: Barrel
162 262, 362, 462: Body
164, 264, 364, 464: Front End
166, 266, 366, 466: Nozzle
168, 268, 368, 468: Nozzle Lumen
170, 270, 370, 470: Second Flanges
172, 272, 372, 472: External Arm Passage
174, 274, 374, 474: Syringe Cavity
176, 276, 376, 476: Circular Prominence
178, 278, 378, 478: Barrel front opening
280: Luer Lock

The invention claimed is:

1. A hand-held syringe configured for integrated aspiration and guidewire operations, comprising:
a plunger having
a seal at a forward end thereof,
a plunger push button at a rear end thereof,
an internal plunger arm attached at a rear end thereof to the plunger push button and to the seal at a forward end thereof, and
an external plunger arm attached at a rear end thereof to the plunger push button, the internal plunger arm being arranged co-axially with the external plunger arm and separated by a gap;
a first flange that extends radially away from the external plunger arm at forward end thereof;
a barrel having a wall having a thickness that is accommodated by the gap, at least a portion of the wall being disposed in the gap between the internal plunger arm and external plunger arm, and a nozzle at a forward end thereof;
a second flange that extends radially away from the barrel at a rear end of the barrel; and
a guidewire tract integrated with at least one of the plunger and the barrel, wherein
the external plunger arm and the internal plunger arm are arcuate.

2. The syringe according to claim 1, wherein the guidewire tract is integral with the barrel and offset from a central longitudinal axis of the barrel.

3. The syringe according to claim 2, further comprising at least a barrel front opening between the guidewire tract and the forward end of the barrel that allow fluid communication between a syringe cavity and a tunnel of guidewire tract.

4. The syringe according to claim 3, further comprising a guidewire tract valve rear to the barrel front opening.

5. The syringe according to claim 2, wherein the second flange extends at least partially around an outer surface of the guidewire tract.

6. The syringe according to claim 2, wherein the plunger push button includes an opening for the guidewire tract.

7. The syringe according to claim 2, wherein the first flange includes a gap for the guidewire tract.

8. The syringe according to claim 1, wherein the nozzle overlaps the guidewire tract and extending beyond a forward end of the barrel, the nozzle including a nozzle lumen that, with the guidewire tract, forms a continuous tunnel along the syringe.

9. The syringe according to claim 1, wherein the guidewire tract is integral with the plunger and the barrel and is coaxial with a central longitudinal axis of the plunger and the barrel.

10. The syringe according to claim 9, wherein the guidewire tract includes a plunger guidewire tract and a barrel guidewire tract that form a continuous tunnel along the syringe.

11. The syringe according to claim 10, further comprising a guidewire tract valve in the plunger guidewire tract in front of the rear opening of guidewire tract.

12. The syringe according to claim 10 further comprising an opening in the seal to allow the plunger guidewire tract and the barrel guidewire tract to extend therethrough.

13. The syringe according to claim 1, wherein the second flange partially overlaps the external plunger arm and includes an external arm passage that allows the external plunger arm to pass therethrough.

14. The syringe according to claim 13, wherein the external plunger arm extends further upward along the barrel than the internal plunger arm and the external arm passage provides a groove that allows the external plunger arm to pass therethrough.

15. The syringe according to claim 1, wherein the external plunger arm includes an introducer that extends forward past the first flange.

16. The syringe according to claim 1, wherein the plunger includes the external plunger arm and another external plunger arm that form a pair of external plunger arms, and the internal plunger arm and another internal plunger arm that form a pair of internal plunger arms, on opposing sides of a central longitudinal axis of the syringe, the pair of external plunger arms and the pair of internal plunger arms each attached at a rear thereof to the plunger push button and having the gap therebetween.

17. The syringe according to claim 16, wherein the first flange includes at least a pair of front flanges, each flange extending radially outwards from a corresponding external plunger arm in a first direction.

18. The syringe according to claim 17, wherein the second flange includes a pair of second flanges, each second flange extending radially outwards from the barrel wall between the pair of external plunger arms in a second direction orthogonal to the first direction.

19. The syringe according to claim 16, each external plunger arm includes a spine protruding therefrom along a central longitudinal direction thereof.

20. The syringe according to claim 1, wherein the external plunger arm and the internal plunger arm have a connector between them at their rear end.

21. The syringe according to claim 20, wherein at least one of the external plunger arm and the internal plunger arm have nubs.

22. The syringe according to claim 1, wherein the plunger push button has an opening corresponding to the internal plunger arm in an inner surface thereof.

23. The syringe according to claim 22, wherein the plunger push button includes a gap to allow the guidewire tract therethrough and a groove on an upper inner surface.

24. The syringe according to claim 1, further comprising:
another external plunger arm wherein the external plunger arm and the another external plunger arm have another gap therebetween that accommodates the guidewire tract.

25. The syringe according to claim 24, wherein the gap has a width that corresponds to a width of an external wall of the guidewire tract.

26. The syringe according to claim 25, wherein an inner surface of the second flange abuts at least partially an outer surface of the guidewire tract.

27. The syringe according to claim 1, further comprising a scale having luminescent indicia on the plunger external arm.

28. The syringe according to claim 1, further comprising a seal support extending from a rear surface of the seal towards the plunger push button.

29. A hand-held syringe, comprising:
a plunger having
a seal at a forward end thereof,
a plunger push button at a rear end thereof,
an internal plunger arm attached at a rear end thereof to the plunger push button and to the seal at a forward end thereof, and
an external plunger arm attached at a rear end thereof to the plunger push button, the internal plunger arm being arranged co-axially with the external plunger arm and separated by a gap;
a first flange that extends radially away from the external plunger arm at the forward end thereof;
a barrel having a wall having a thickness that is accommodated by the gap, at least a portion of the wall being disposed in the gap between the internal plunger arm and external plunger arm, and a nozzle at a forward end thereof; and
a second flange that extends radially away from the barrel at a rear end thereof, wherein the second flange partially overlaps the external plunger arm and includes an external arm passage that allows the external plunger arm to pass therethrough wherein
the external plunger arm and the internal plunger arm are both arcuate, and have a connector between them at their rear end that maintains the gap between the external plunger arm and the internal plunger arm.

* * * * *